United States Patent
Dorros et al.

(10) Patent No.: US 7,063,714 B2
(45) Date of Patent: Jun. 20, 2006

(54) APPARATUS AND METHODS FOR TREATING STROKE AND CONTROLLING CEREBRAL FLOW CHARACTERISTICS

(75) Inventors: Gerald Dorros, Scottsdale, AZ (US); Juan Carlos Parodi, Buenos Aires (AR); Claudio Javier Schönholz, Shreveport, LA (US); Michael Hogendijk, Palo Alto, CA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 553 days.

(21) Appl. No.: 09/972,225

(22) Filed: Oct. 4, 2001

(65) Prior Publication Data

US 2003/0040704 A1    Feb. 27, 2003

Related U.S. Application Data

(60) Provisional application No. 60/314,269, filed on Aug. 22, 2001.

(51) Int. Cl.
   *A61M 29/00*    (2006.01)
(52) U.S. Cl. .................. 606/194; 604/96.01; 604/523; 604/101.04
(58) Field of Classification Search .............. 604/106, 604/96.01, 4.01, 6.1, 6.16, 101.02, 264, 915, 604/523, 528, 919, 103, 271, 101.04, 101.05; 606/192, 194, 191
See application file for complete search history.

(56) References Cited

U.S. PATENT DOCUMENTS

| | | | |
|---|---|---|---|
| 5,794,629 A | | 8/1998 | Frazee |
| 5,895,398 A | | 4/1999 | Wensel et al. |
| 5,908,407 A | | 6/1999 | Frazee et al. |
| 5,972,019 A | | 10/1999 | Engelson et al. |
| 6,022,336 A | * | 2/2000 | Zadno-Azizi et al. .. 604/101.05 |
| 6,044,845 A | | 4/2000 | Lewis |
| 6,105,582 A | | 8/2000 | Pranevicius et al. |
| 6,110,139 A | | 8/2000 | Loubser |
| 6,135,991 A | * | 10/2000 | Muni et al. ................. 604/509 |
| 6,146,370 A | | 11/2000 | Barbut |
| 6,161,547 A | * | 12/2000 | Barbut ....................... 128/898 |
| 6,165,199 A | * | 12/2000 | Barbut ....................... 606/200 |
| 6,231,551 B1 | | 5/2001 | Barbut |
| 6,533,800 B1 | * | 3/2003 | Barbut ....................... 606/194 |
| 6,555,057 B1 | * | 4/2003 | Barbut et al. ................. 422/44 |
| 6,595,980 B1 | * | 7/2003 | Barbut ....................... 604/509 |
| 2002/0165573 A1 | * | 11/2002 | Barbut ....................... 606/194 |

* cited by examiner

Primary Examiner—Cris Rodriguez
(74) Attorney, Agent, or Firm—Kevin J. Boland

(57) ABSTRACT

Apparatus and methods for treatment of stroke are provided. In a preferred embodiment, the present invention disposes at least one catheter having a distal occlusive member in either the common carotid artery (CCA) or both the vertebral artery (VA) and the CCA on the hemisphere of the cerebral occlusion. Blood flow in the opposing carotid and/or vertebral arteries may be inhibited. Retrograde or antegrade flow may be provided through either catheter independently to effectively control cerebral flow characteristics. Under such controlled flow conditions, a thrombectomy device may be used to treat the occlusion, and any emboli generated are directed into the catheter(s).

22 Claims, 20 Drawing Sheets

APPARATUS AND METHODS FOR TREATING STROKE AND CONTROLLING CEREBRAL FLOW CHARACTERISTICS

FIELD OF THE INVENTION

The present invention relates to improved apparatus and methods for treatment of stroke. More specifically, the apparatus and methods of the present invention are directed to treating stroke by controlling cerebral blood flow and removing thrombi and/or emboli.

BACKGROUND OF THE INVENTION

Cerebral occlusions that lead to stroke require swift and effective therapy to reduce morbidity and mortality rates associated with the disease. Many current technologies for treating stroke are inadequate because emboli generated during the procedure may travel downstream from the original occlusion and cause ischemia. There is currently a need for a stroke treatment system that provides a swift and efficient treatment for occlusions while simultaneously controlling cerebral flow characteristics.

In the initial stages of stroke, a CT scan or MRI may be used to diagnose the cerebral occlusion, which commonly occurs in the middle cerebral arteries. Many current technologies position a catheter proximal to the occlusion, then deliver clot dissolving drugs to treat the lesion. A drawback associated with such technology is that delivering drugs may require a period of up to six hours to adequately treat the occlusion. Another drawback associated with lytic agents (i.e., clot dissolving agents) is that they often facilitate bleeding.

When removing thrombus using mechanical embolectomy devices, it is beneficial to engage the thrombus and remove it as cleanly as possible, to reduce the amount of emboli that are liberated. However, in the event that emboli are generated during mechanical disruption of the thrombus, it is imperative that they be subsequently removed from the vasculature.

Many current drug delivery and mechanical treatment methods are performed under antegrade flow conditions. Such treatment methods do not attempt to manipulate flow characteristics in the cerebral vasculature, e.g, the Circle of Willis and communicating vessels, such that emboli may be removed. Accordingly, there remains a need to provide effective thrombus and emboli removal from the cerebral vasculature while simultaneously controlling flow within that vasculature.

U.S. Pat. No. 6,161,547 to Barbut (Barbut '547) describes a technique for enhancing flow in the cerebral vasculature in treating patients with acute stroke or other cerebrovascular disease. The technique involves: (1) positioning a first tubular member in a vascular location suitable for receiving antegrade blood flow; (2) positioning a second tubular member in a contralateral artery of the occlusion (e.g., for an occlusion located in the left common carotid artery the second tubular member is placed in the right common carotid artery); and coupling the first tubular member to the second tubular member using a pump and filter.

The first tubular member receives antegrade blood flow and channels the blood to the pump and filter, where the blood then is reperfused via the second tubular member into the contralateral artery, thus increasing blood flow to the opposing hemisphere of the brain. The first and second tubular members may include balloons disposed adjacent to their distal ends.

The techniques described in the foregoing patent have several drawbacks. For example, if the first balloon of the first tubular member is deployed in the left common carotid artery, as shown in FIG. 7C, aspiration of blood from the vessel between the balloon and the occlusion may cause the vessel to collapse. On the other hand, if the balloon is not deployed, failure to stabilize the distal tip may result in damage to the vessel walls. In addition, failure to occlude the vessel may permit antegrade blood flow to diverted into that apparatus, rather than blood distal to the first tubular member.

The Barbut '547 patent further discloses that inflating the balloon of the second tubular member may assist in controlling the flow to the contralateral artery or provide more efficient administration of pharmacotherapy to the cerebral tissues. However, when that balloon is deployed, the contralateral artery may be starved of sufficient flow, since the only other flow in that artery is that aspirated through the first tubular member. On the other hand, if the balloon of the second tubular member is not inflated, no flow control is possible.

A method for removing cerebral occlusions is described in U.S. Pat. No. 6,165,199 to Barbut (Barbut '199). This patent describes a catheter having an aspiration port at its distal end that communicates with a vacuum at its proximal end. A perfusion port disposed in a lateral surface of the catheter may be used to enhance antegrade flow in collateral arteries. In use, the aspiration port is positioned proximal to an occlusion to provide a direct suction effect on the occlusion. The perfused flow in collateral arteries is intended to augment retrograde flow distal to the occlusion, such that the occlusion is dislodged via the pressure and directed toward the aspiration port. A chopping mechanism, e.g., an abrasive grinding surface or a rotatable blade, coupled to the aspiration port recognizes when the aspiration port is clogged. The chopping mechanism then engages to break up the occlusion and permit it to enter the aspiration port in smaller pieces.

The device described in the Barbut '199 patent has several disadvantages. First, the use of a vacuum to aspirate the occlusion requires an external pressure monitoring device. The application of too much vacuum pressure through the aspiration port may cause trauma, i.e., collapse, to the vessel wall. Also, because the system is intended to dislodge the occlusion using a pressure differential, a chopping mechanism is required to prevent the entire mass from clogging the aspiration port. The use of a chopping mechanism, however, may generate such a large quantity of emboli that it may be difficult to retrieve all of the emboli. In addition, emboli generated by the action of the chopping mechanism may accumulate alongside the catheter, between the aspiration port and the distal balloon. Once this occurs, it is unclear how the emboli will be removed.

Yet another drawback of the device described in the Barbut '199 patent is that high-pressure perfusion in collateral arteries may not augment retrograde flow distal to the occlusion as hypothesized. The patent indicates that high-pressure perfusion in collateral arteries via side ports in the catheter may be sufficient to cause an increase in pressure distal to the occlusion. Antegrade blood flow from the heart in unaffected arteries, e.g., other vertebral and/or carotid arteries, may make it difficult for the pressure differential induced in the contralateral arteries to be communicated back to the occluded artery in a retrograde fashion.

Other methods for treating ischemic brain stroke have involved cerebral retroperfusion techniques. U.S. Pat. No. 5,794,629 to Frazee describes a method that comprises at least partially occluding the first and second transverse venous sinuses and introducing a flow of the patient's arterial blood to a location distal to the partial venous occlusions. As described in that patent, the infusion of arterial blood into the venous sinuses provides a retrograde venous flow that traverses the capillary bed to oxygenate the ischemic tissues and at least partially resolve ischemic brain symptoms.

One drawback associated with the technique described in the Frazee patent is that the pressure in the transverse venous sinuses must be continuously monitored to ensure that cerebral edema is avoided. Because the veins are much less resilient than arteries, the application of sustained pressure on the venous side may cause brain swelling, while too little pressure may result in insufficient blood delivered to the arterial side.

In addition to the foregoing methods to augment cerebral perfusion, several methods are known for mechanically removing clots to treat cerebral occlusions. U.S. Pat. No. 5,895,398 to Wensel et al. describes a shape-memory coil affixed to an insertion mandrel. The coil is contracted to a reduced profile state within the lumen of a delivery catheter, and the catheter is used to cross a clot. Once the coil is disposed distal to the clot, the coil id deployed. The coil then is retracted proximally to engage and remove the clot.

A primary drawback associated with the Wensel device is that the deployed coil contacts the intima of the vessel, and may damage to the vessel wall when the coil is retracted to snare the occlusion. Additionally, the configuration of the coil is such that the device may not be easily retrieved once it has been deployed. For example, once the catheter has been withdrawn and the coil deployed distal to the occlusion, it will be difficult or impossible to exchange the coil for another of different dimensions.

U.S. Pat. No. 5,972,019 to Engelson et al. describes a deployable cage assembly that may be deployed distal to a clot. Like the Wensel device, the Engelson device is depicted as contacting the intima of the vessel, and presents the same risks as the Wensel device. In addition, because the distal end of the device comprises a relatively large profile, the risk of dislodging emboli while crossing the clot is enhanced, and maneuverability of the distal end of the device through tortuous vasculature may be reduced.

In view of these drawbacks of previously known clot removal apparatus and methods, it would be desirable to provide apparatus and methods for controlling hemodynamic properties at selected locations in the cerebral vasculature, e.g., the Circle of Willis and communicating vessels.

It also would be desirable to provide apparatus and methods for removal and recovery of thrombi and/or emboli above the carotid bifurcation.

It still further would be desirable to provide apparatus and methods that quickly and efficiently treat cerebral occlusions.

It still further would be desirable to provide apparatus and methods for selectively providing retrograde and/or antegrade flow to desired regions in the cerebral vasculature to effectively remove emboli.

SUMMARY OF THE INVENTION

In view of the foregoing, it is an object of the present invention to provide apparatus and methods for controlling hemodynamic properties at selected locations in the cerebral vasculature.

It is also an object of the present invention to provide apparatus and methods for removal and recovery of thrombi and/or emboli above the carotid bifurcation.

It is a further object of the present invention to provide apparatus and methods that quickly and efficiently treat cerebral occlusions.

It still a further object of the present invention to provide apparatus and methods for selectively providing retrograde and/or antegrade flow to desired regions in the cerebral vasculature to effectively remove emboli.

These and other objects of the present invention are accomplished by providing a stroke treatment system comprising an emboli removal catheter and one or more flow control devices suitable for manipulating blood flow in the cerebral vasculature. The stroke treatment system may facilitate the introduction and subsequent removal of clot lysing agents, or further comprise a thrombectomy element.

In a preferred embodiment, the emboli removal catheter is transluminally inserted and disposed in the common carotid artery CCA, and comprises a flexible catheter having an occlusive member disposed on its distal end. The occlusive member is configured to be deployed to anchor the catheter and occlude antegrade flow in the CCA. A separate occlusive element is configured to pass through a lumen of the emboli removal catheter, and is deployed in the external carotid artery ECA to occlude flow through that vessel.

One or more flow control devices, each having a rapidly deployable occlusive member, then are positioned at selected locations, e.g., in the subclavian arteries, and may be deployed to isolate or redistribute flow through the cerebral vasculature. Preferably, the flow control devices occlude blood flow in the vertebral and carotid arteries in the hemisphere in which the occlusion is not located. This temporarily influences flow in the opposing hemisphere. Preferably, the flow control devices are provided in sufficient number that, when deployed, the flow control devices substantially influence the flow dynamic of mid-cerebral artery.

Once the foregoing components have been deployed, a lysing agent may be introduced into the vessel through a lumen of the emboli removal catheter. After an appropriate period, the occlusive members on one or more of the flow control devices may be collapsed to cause retrograde flow through the cerebral vasculature sufficient to flush the lysing agent and any emboli or debris from the vasculature into the emboli removal catheter. The stroke treatment system and flow control devices may then be withdrawn from the patient's vasculature.

Alternatively, a thrombectomy element may be advanced transluminally via the ICA to a position just proximal of a cerebral occlusion, e.g., in the middle cerebral artery, after placement (but prior to deployment) of the flow control devices. The flow control devices then are deployed to selectively and temporarily redistribute or suspend flow in the cerebral vasculature. The thrombectomy element preferably is advanced to the site of the cerebral occlusion through a lumen of the emboli removal catheter.

With flow controlled throughout the Circle of Willis and therefore the communicating mid-cerebral artery, the thrombectomy element then is engaged with the lesion. Actuation of the thrombectomy element preferably causes mechanical disruption of the emboli or thrombus, after which the element is retracted into the emboli removal catheter. By selectively de-actuating one or more of the flow control devices, retrograde or redistributed flow may be generated in the vasculature that cases emboli liberated during actuation of the thrombectomy element to be directed into the emboli removal catheter. The flow control devices then are withdrawn to reestablish antegrade blood flow.

In a further alternative embodiment, a second emboli removal catheter may be disposed in a vertebral artery in lieu of one of the flow control devices. In this embodiment, the lumen of the second emboli removal catheter may be perfused with blood or saline under pressure to induce retrograde flow elsewhere in the cerebral vasculature, such as in the carotid or vertebral arteries. Additionally, chilled blood and/or drug agents may be delivered via the second catheter to induce mild hypothermia and/or altered pressure gradients at selected cerebral locations.

The second emboli removal catheter may be used to enhance flow manipulation in the Circle of Willis and communicating vessels to facilitate removal of emboli via either retrograde or antegrade flow either independently or, or simultaneously with, use of the first emboli removal catheter.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
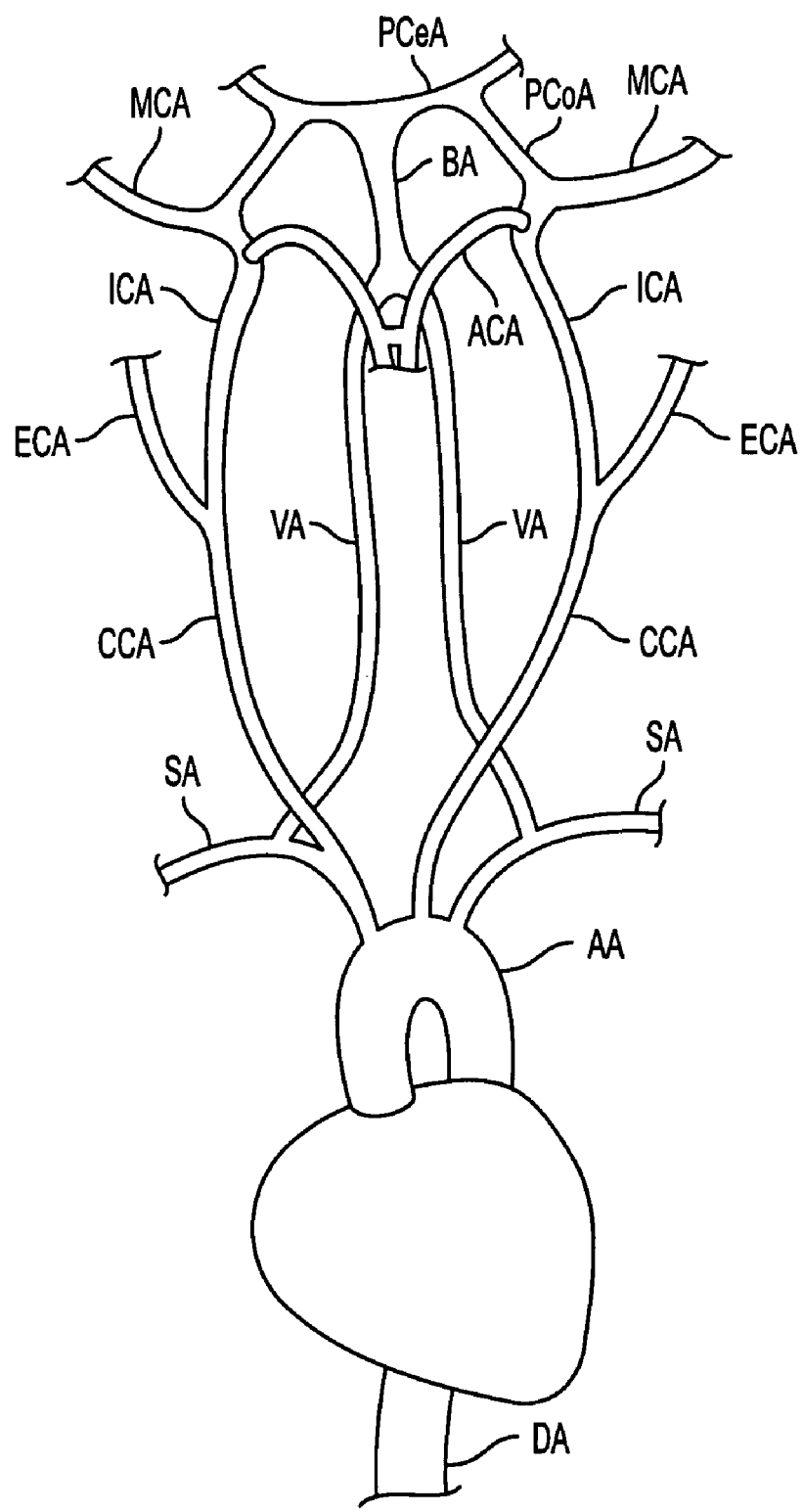
FIG. 1 provides a schematic overview of the portion of the vasculature in which the apparatus and methods of the present invention are intended for use.

Referring to FIG. 1, a schematic of the pertinent vasculature relating to the present invention is provided. Many cerebral obstructions that lead to stroke reside in the middle cerebral arteries MCA. To treat obstructions in the MCA, one approach involves percutaneously and transluminally advancing a therapeutic device to the site of the obstruction via the internal carotid artery ICA.

It is well known in the art to percutaneously and transluminally advance a catheter in retrograde fashion toward coronary vasculature, e.g., via the femoral artery, external iliac artery, descending aorta DA and aortic arch AA. To access cerebral vasculature, including obstructions residing in the MCA, one approach is to further advance a catheter and/or therapeutic devices in antegrade fashion from the aortic arch AA, into the common carotid artery CCA, up through the ICA and into the middle cerebral artery MCA, as shown in FIG. 1.

Treating occlusions in the MCA may generate emboli upon removal of the occlusion. Under normal blood flow conditions, such emboli may travel downstream from the original occlusion and cause ischemia. Accordingly, it is advantageous to manipulate blood flow characteristics in the cerebral vasculature to ensure that emboli generated in the MCA are effectively removed.

The present invention manipulates cerebral blood flow by inhibiting flow from the heart into any of the vertebral arteries VA and common carotid arteries CCA. This may be achieved by disposing flow control devices in the subclavian arteries SA and/or brachiocephalic trunk BT, to temporarily inhibit flow from the aortic arch AA into any of the vertebral arteries VA and common carotid arteries CCA. This interruption of antegrade flow may advantageously alter flow in the Circle of Willis, as described hereinbelow.

Figure 2:
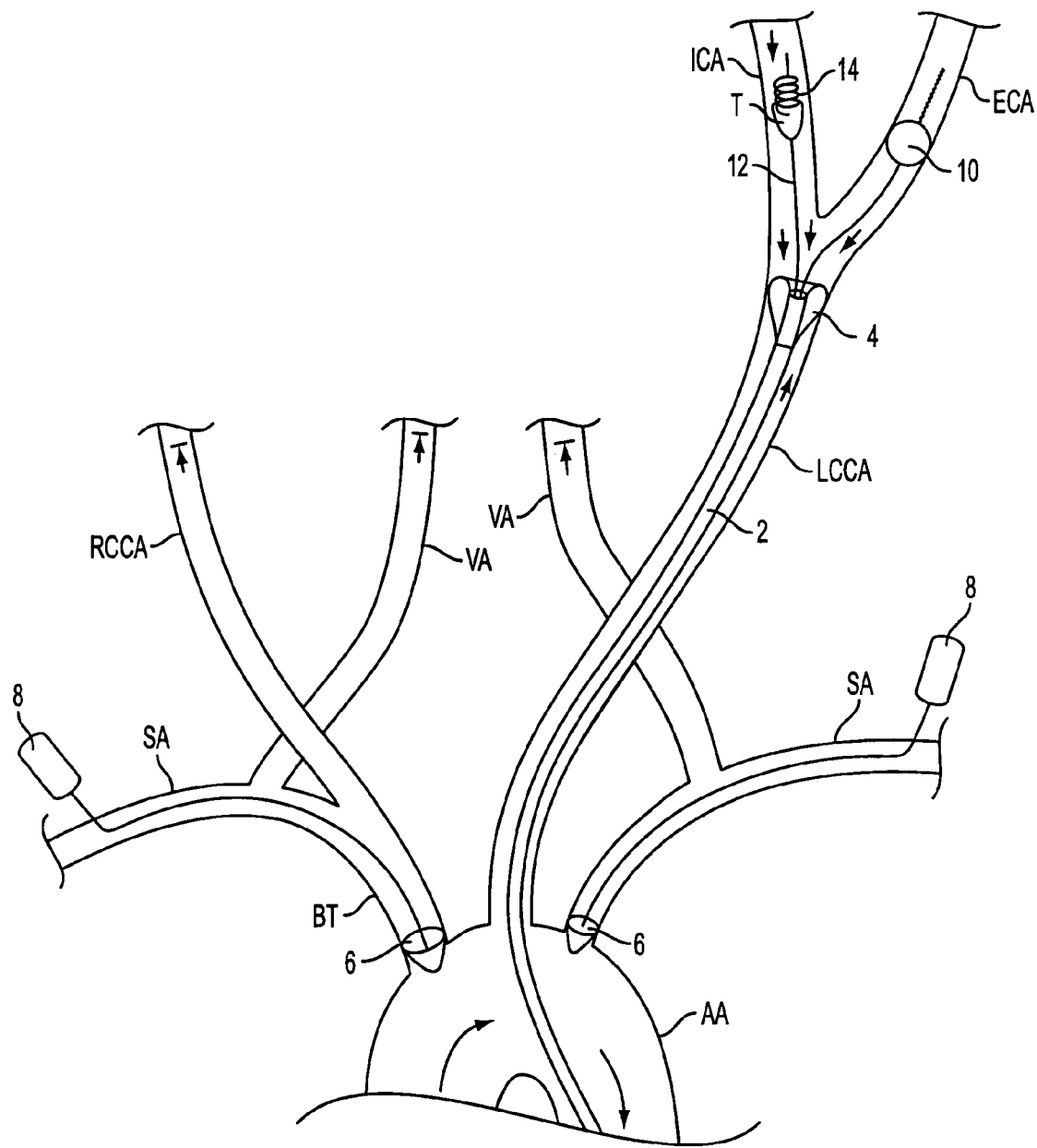
FIG. 2 provides an overview of the apparatus of the present invention deployed in a patient's vasculature.

FIG. 2 provides an overview of the components of the system of the present invention, each of which are described in greater detail hereinbelow.

Flow control devices 8 having occlusive elements 6 are configured to be introduced into the patient's vasculature, e.g., via the radial or brachial arteries. When so positioned, occlusive elements 6 preferably are positioned in the patient's left subclavian artery SA and brachiocephalic trunk BT, as shown. Occlusive elements 6 may have any of a number of designs, with low profile mechanically self-expanding designs being preferred.

Emboli removal catheter 2 includes distal occlusive element 4, and is configured to be percutaneously advanced in retrograde fashion through the descending aorta. Occlusive element 4 preferably comprises a pear-shaped or funnel-shaped balloon as described in copending and commonly assigned U.S. patent application Ser. No. 09/418,727, which is incorporated herein by reference. Occlusive element 4 preferably is positioned proximal to the carotid bifurcation, and then deployed to induce retrograde flow in the ICA by use of a venous return catheter (not shown) that communicates with the proximal end of catheter 2. Balloon 10, also described in the foregoing application, is deployed in the ECA to ensure that retrograde flow from the ICA is not carried in an antegrade fashion into the ECA.

Flow control devices 8 and emboli removal catheter 2 are used to suspend antegrade flow in the cerebral arteries and to selectively suspend or redistribute flow in the cerebral vasculature. Once so-deployed, a lysing agent may be introduced to dissolve the clot, followed by selectively contracting one or more of the flow control devices to induce retrograde flow through emboli removal catheter 2.

Alternatively, after placement of flow control devices 8, but before they are deployed, thrombectomy wire 12 may be introduced into the vessel containing the lesion. Flow control devices 8 then may be deployed, as shown in FIG. 2, to prevent flow from the aortic arch AA into the right common carotid artery RCCA and the right and left vertebral arteries VA. Such selective manipulation of flow into the carotid and/or vertebral arteries alters flow characteristics in the cerebral vasculature, and permits retrograde flow through to be induced to flush emboli and debris into the lumen of catheter 2 for removal.

In the embodiment of FIG. 2, thrombectomy wire 12 comprises knot 14 that is deployed distal to the thrombus T. Thrombectomy wire 12 and thrombus T then are retracted proximally into the lumen of emboli removal catheter 2, and any embolic fragments generated during this procedure are directed into catheter 2 by inducing localized retrograde flow. Once the thrombus is removed, flow control devices 8 are contracted to reestablish flow to the cerebral vasculature.

Figure 3A:
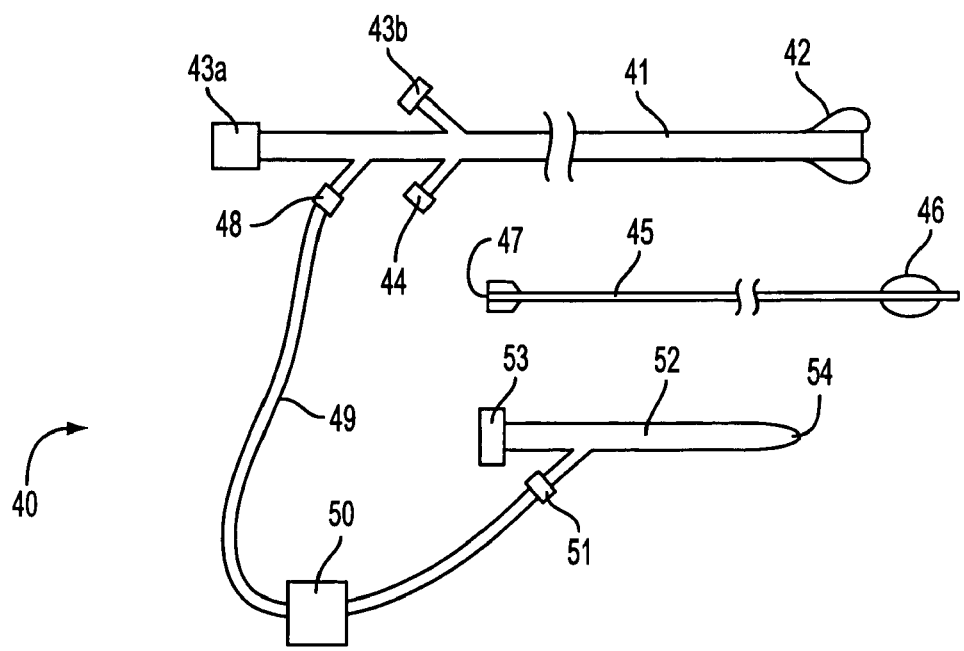
FIGS. 3A–3D are, respectively, a schematic view, and detailed side and sectional views of the distal end of an emboli removal catheter of the present invention.

Referring now to FIG. 3A, stroke treatment apparatus 40 constructed in accordance with the principles of the present invention is described. Apparatus 40 comprises emboli removal catheter 41, wire 45, venous return line 52, tubing 49 and optional blood filter 50.

Catheter 41 includes distal occlusive element 42, hemostatic ports 43a and 43b, e.g., Touhy-Borst connectors, inflation port 44, and blood outlet port 48. Wire 45 includes balloon 46 that is inflated via inflation port 47. Tubing 49 couples blood outlet port 48 to filter 50 and blood inlet port 51 of venous return line 52.

Wire 45 preferably comprises a small diameter flexible shaft having an inflation lumen that couples inflatable balloon 46 to inflation port 47. Wire 45 and balloon 46 are configured to pass through hemostatic ports 43a and 43b and the aspiration lumen of catheter 41 (see FIGS. 3C and 3D), so that balloon 46 may be disposed in a communicating artery, e.g., the external carotid artery. Ports 43a and 43b and the aspiration lumen of catheter 41 are sized to permit additional interventional devices, such as thrombectomy wires, to be advanced through the aspiration lumen when wire 45 is deployed.

Venous return line 52 includes hemostatic port 53, blood inlet port 51 and a lumen that communicates with ports 53 and 51 and tip 54. Venous return line 52 may be constructed in a manner per se known for venous introducer catheters. Tubing 49 may comprise a suitable length of a biocompatible material, such as silicone. Alternatively, tubing 49 may be omitted and blood outlet port 48 of catheter 41 and blood inlet port 51 of venous return line 52 may be lengthened to engage either end of filter 50 or each other.

Figure 3B:
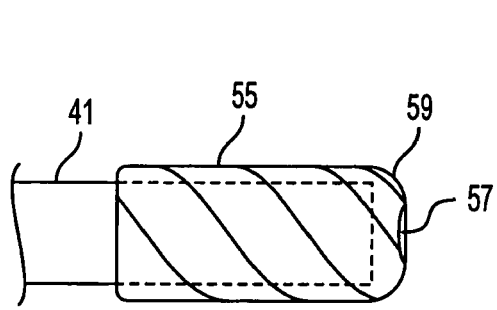
Figure 3C:
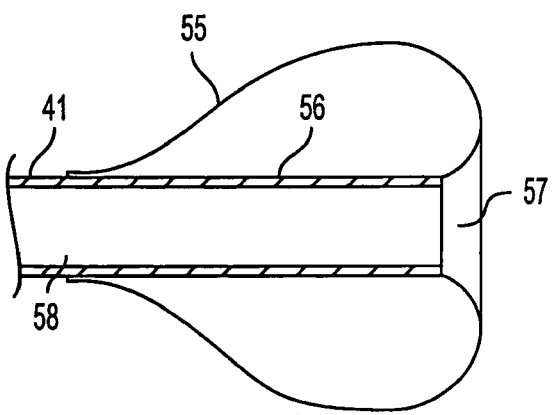

With respect to FIGS. 3B and 3C, distal occlusive element 42 comprises expandable funnel-shaped balloon 55. In accordance with manufacturing techniques which are known in the art, balloon 55 comprises a compliant material, such as polyurethane, latex or polyisoprene which has variable thickness along its length to provide a funnel shape when inflated. Balloon 55 is affixed to distal end 56 of catheter 41 in an inverted fashion, for example, by gluing or a melt-bond, so that opening 57 in balloon 55 leads into aspiration lumen 58 of catheter 41. Balloon 55 preferably is wrapped and heat treated during manufacture so that distal portion 59 of the balloon extends beyond the distal end of catheter 41 and provides an atraumatic tip or bumper for the catheter.

Figure 3D:
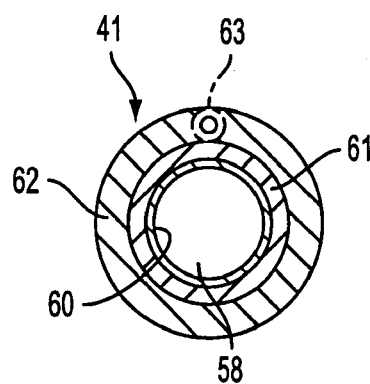

As shown in FIG. 3D, catheter 41 preferably comprises inner layer 60 of low-friction material, such as polytetrafluoroethylene ("PTFE"), covered with a layer of flat stainless steel wire braid 61 and polymer cover 62 (e.g., polyurethane, polyethylene, or PEBAX). Inflation lumen 63 is disposed within polymer cover 62 and couples inflation port 44 to balloon 55.

Referring to FIGS. 4, features of the flow control devices of the present invention are described. The flow control devices may comprise either an inflatable balloon or a mechanically deployable mechanism. In FIG. 4A, a preferred embodiment of the proximal end for a mechanically deployable mechanism comprises controller 70, delivery port 78, e.g., for delivering cardioplegic agents, deployment knob 72 that is configured to slide within slot 74, and guidewire lumen 76, which may comprise a self-sealing valve. Body 73 houses a plurality of lumens, e.g., a mechanical deployment lumen, a therapeutic drug delivery lumen, and a guidewire lumen. In an alternative embodiment, for use in conjunction with an inflatable balloon, port 78 may serve as an inflation/aspiration port while deployment knob 72 and slot 74 are omitted.

Figure 4A:
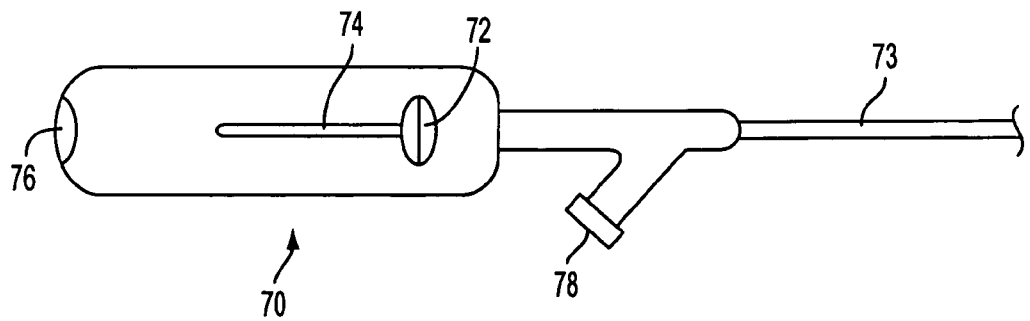
FIGS. 4A–4E provide detailed views of the proximal and alternative distal ends of the flow control devices of the present invention contracted and expanded states.
Figure 4B:
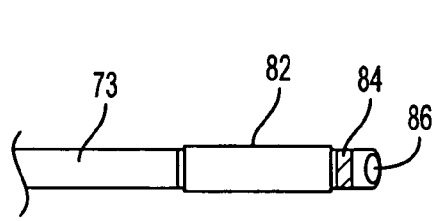
Figure 4C:
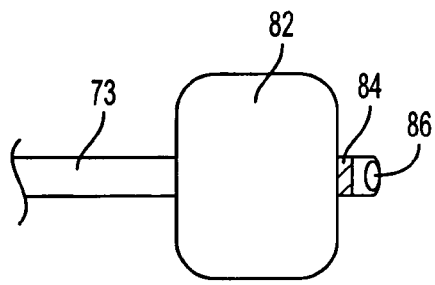

FIGS. 4B–4C illustrate the distal end of the flow control device having inflatable balloon 82 in contracted and deployed states, respectively. In use, body 73 is advanced over a guidewire via guidewire lumen 86. Radiopaque tip marker 84 may be used to aid in fluoroscopically guiding the device. Balloon 82 then is inflated by a lumen within body 73 that communicates with port 78. Port 78 may communicate with a timing mechanism (not shown) that automatically deflates balloon 82 after a predetermined time, e.g., 15 seconds, to ensure that cerebral blood flow is not inhibited for a period so long as to cause cerebral compromise.

Figure 4D:
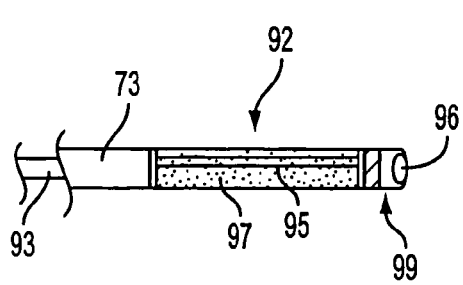
Figure 4E:
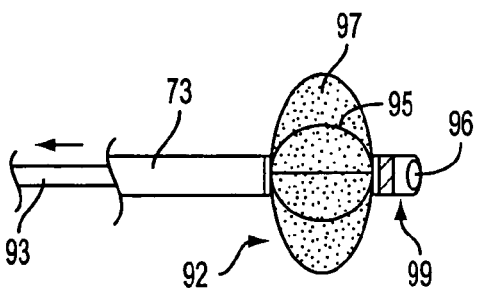

FIGS. 4D–4E illustrate mechanically deployable mechanism 92 comprising flexible wires 95 and impermeable coating 97 in contracted and deployed states, respectively. Impermeable coating 97 comprises an elastomeric polymer, e.g., latex, polyurethane or polyisoprene. The proximal end of deployable mechanism 92 is affixed to body 73. The distal end of mechanism 92 is affixed to distalmost section 99, which in turn communicates with sliding member 93 that is configured to slide longitudinally within a lumen of body 73.

Upon actuating deployment knob 72, i.e., proximally retracting knob 72 within slot 74, sliding member 93 and distalmost section 99 are proximally retracted relative to body 73, to compress flexible wires 95. Impermeable coating 97 conforms to the shape of wires 95 to provide a plug-shaped occlusive member, as shown in FIG. 4E. Deployment knob 72 may communicate with a timing mechanism (not shown) that automatically releases mechanism 92 after a predetermined time.

Figure 5A:
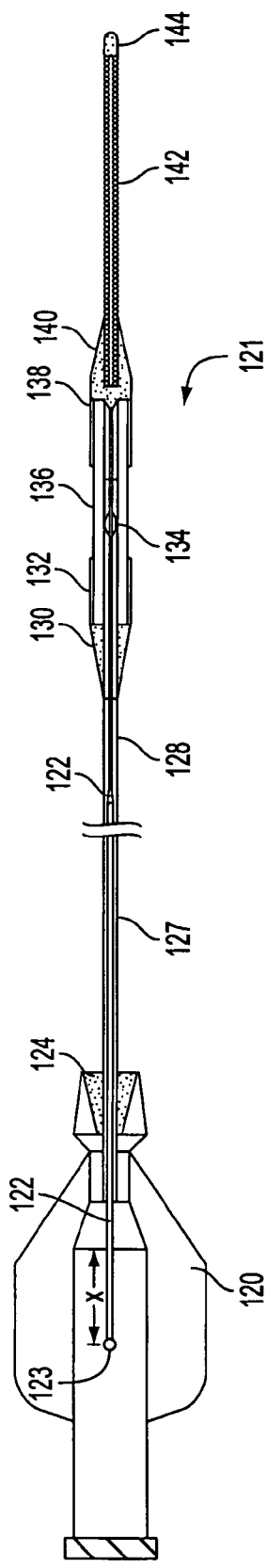
FIGS. 5A–5B are views of alternative embodiments of low profile occlusive elements for occluding flow in the external carotid arteries.

Referring to FIGS. 5, alternative embodiments for guide wire 45 and balloon 46 of FIG. 3A are described for use in occluding a communicating artery, e.g., the external carotid artery. In FIG. 5A, occlusive device 121 comprises proximal hub 120, hypo tube 127, shaft 128, balloon 136 and coil 142. Hypo tube 127 preferably comprises stainless steel, while shaft 128 preferably comprises a radiopaque material. Balloon 136 is configured using a tubular balloon material, e.g., chronoprene, that is compliant in nature and provides a self-centering balloon when deployed. The proximal end of balloon 136 is secured to radiopaque shaft 128 by band 132 and taper 130. The distal end of balloon 136 is affixed to coil 142 via taper 140.

Core wire 122 is slidably disposed within hypo tube 127 so that its proximal end is disposed in proximal hub 120 and its distal end is affixed to taper 140. Fluid may be injected into the annulus surrounding core wire 122 so that the fluid exits into balloon 136 via inflation window 134, thus permitting balloon 136 to expand radially and longitudinally. Core wire 122, taper 140 and coil 142 may move distally to accommodate such linear extension. Stroke limiter 123, disposed on the distal end of core wire 122, ensures that balloon 136 does not extend longitudinally more a predetermined distance 'x'.

Figure 5B:
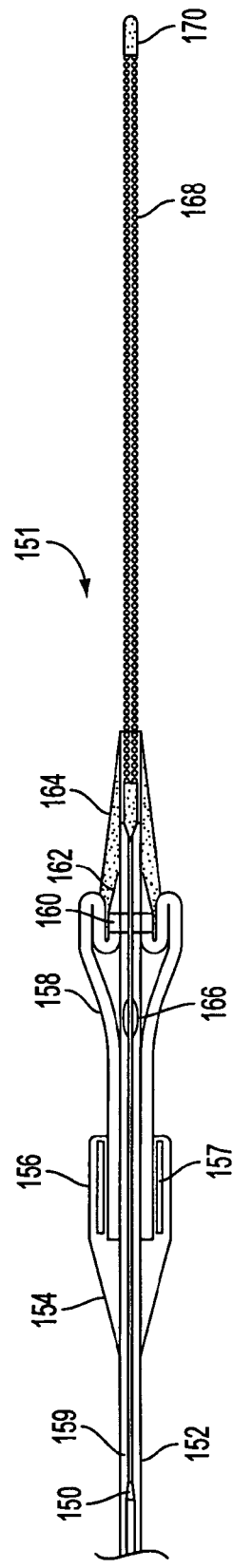

In the alternative embodiment of FIG. 5B, occlusive device 151 comprises shaft 152, balloon 158, and coil 168. Shaft 152 preferably comprises a radiopaque material and connects to a hypo tube similar to that of FIG. 5A. The proximal components for device 151, i.e., proximal to shaft 152, are the same as the components that are proximal to shaft 128 in FIG. 5A.

Balloon 158 is constrained at its proximal end by band 156 having proximal balloon marker 157. Taper 154 is provided on the proximal end of band 156 in alignment with the proximal end of balloon 158. The distal end of balloon 158 is everted, as shown in FIG. 5B, and secured with radiopaque band 160 that provides a fluoroscopic reference for the distal boundary of the balloon. Taper 164 further secures the everted distal section, sandwiching between the first and second folds.

Core wire 150 is distally affixed to coil 168 having radiopaque marker 170. Lumen 159 communicates with an inflation port (not shown) at its proximal end and with inflation window 136 at its distal end. Lumen 159 permits the injection of fluids, e.g., saline, to deploy balloon 158. Core wire 150 is slidably disposed in the hypo tube and shaft 152 to prevent extension of balloon 158 up to a distance 'x', as indicated in FIG. 5A.

Referring to FIGS. 6, apparatus suitable for removing thrombi are described. In FIG. 6A, thrombectomy wire 200 having ball 202 affixed to its distal end is depicted in a contracted state within coil 204. In a preferred embodiment, thrombectomy wire 200 comprises a shape-memory retaining material, for example, a Nickel Titanium alloy (commonly known in the art as Nitinol).

The use of Nitinol generally requires the setting of a custom shape in a piece of Nitinol, e.g., by constraining the Nitinol element on a mandrel or fixture in the desired shape, and then applying an appropriate heat treatments, which are per se known.

Coil 204 covers wire 202 along its length, up to ball 202. As coil 204 is retracted proximally, wire 200 self-expands to a predetermined knot configuration, as shown in FIG. 6B. In a preferred embodiment, the diameter of wire 200 is about 0.002 inches, the diameter of ball 202 is about 0.014 inches, and coil 204 is manufactured using platinum. It should be appreciated that an outer sheath may be used in place of coil 204, such that proximally retracting the outer sheath causes wire 200 to deploy.

Figure 6A:
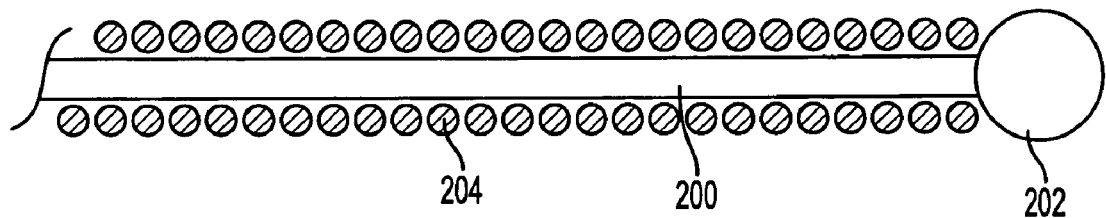
FIGS. 6A–6F depict thrombectomy wires having shape memory properties in contracted and deployed states.
Figure 6B:
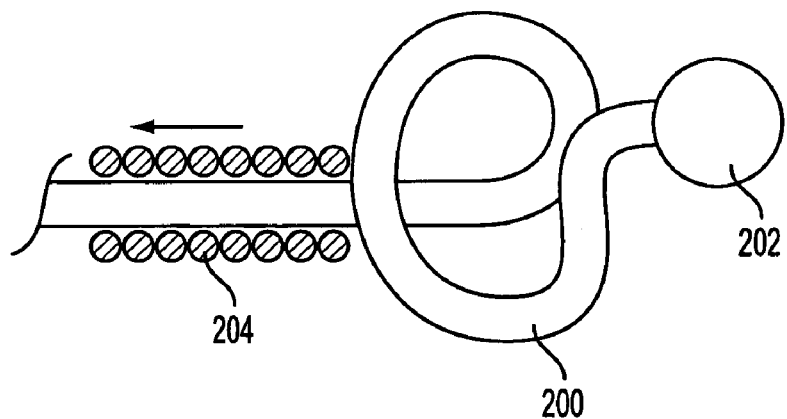
Figure 6C:
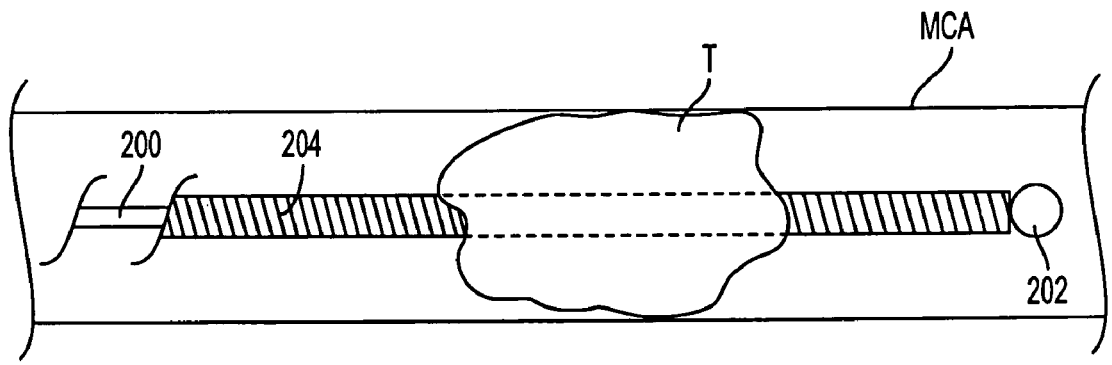

Referring to FIG. 6C, a method for using thrombectomy wire 200 to snare a thrombus T, e.g., in middle cerebral artery MCA, is described. Thrombectomy wire 200, initially contracted within coil 204, is advanced through a lumen of catheter 2, then preferably is advanced in retrograde fashion via the internal carotid to the site of the cerebral lesion in the MCA. Under controlled flow conditions, i.e., conditions that will promote the flow of emboli toward catheter 2, wire 200 and coil 204 pierce thrombus T, as shown in FIG. 6C.

Figure 6D:
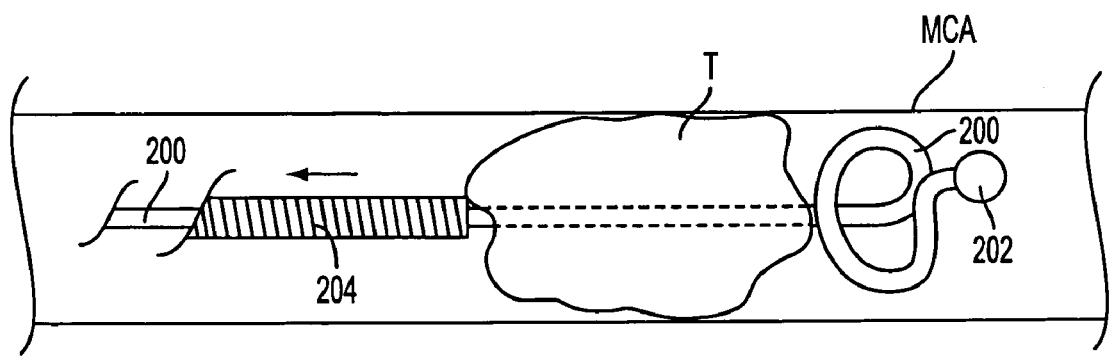

Coil 204 then is retracted proximally with respect to wire 200 to self-deploy shape memory wire 200 at a location distal to thrombus T, as shown in FIG. 6D. Wire 200 then is retracted to snare thrombus T, and ball 202 of wire 200 facilitates removal of the lesion.

Figure 6E:
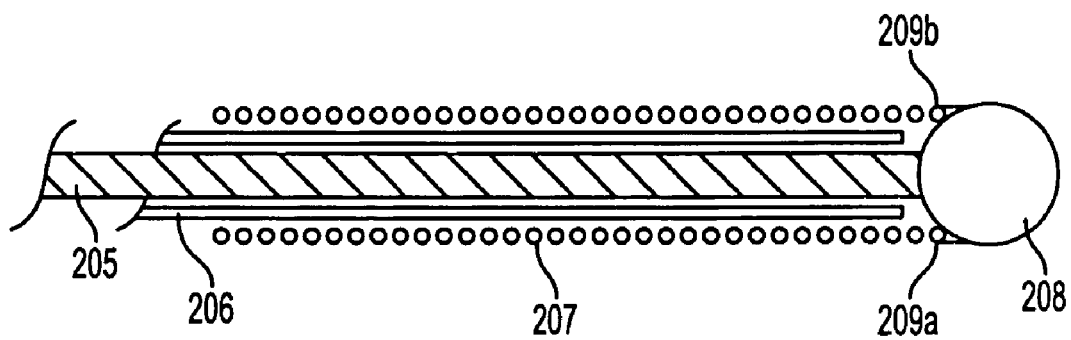
Figure 6F:
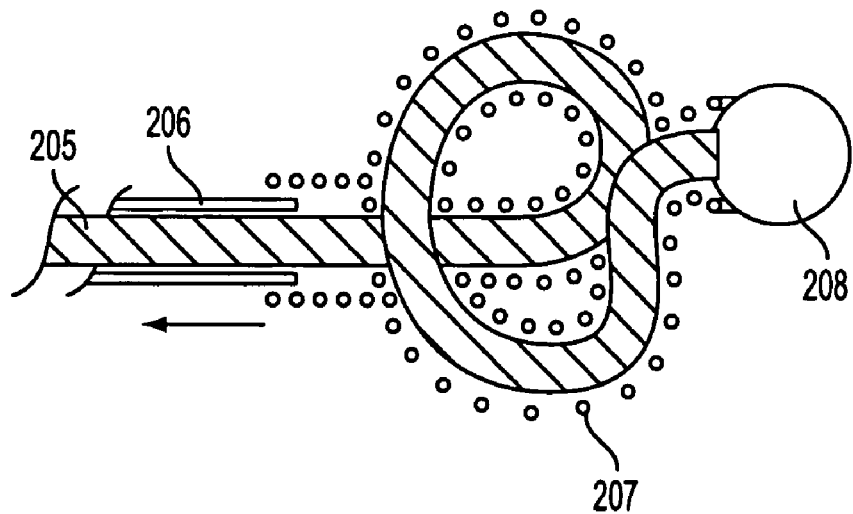

Referring to FIGS. 6E–6F, an alternative embodiment a thrombectomy wire of FIGS. 6A–B is described. In FIG. 6E, thrombectomy wire 205 having distal ball 208 is delivered in a contracted state within slidable sheath 206. Thrombectomy wire 205 is configured to self-deploy to a predetermined shape, e.g., via use of a shape memory material, upon proximal retraction of sheath 206. Coil 207 overlays slidable sheath 206 and is affixed to ball 208 at points 209a and 209b, e.g., via a solder or weld. Sheath 206 is initially provided in a distalmost position such that it abuts ball 208 and constrains wire 205 along its length. Sheath 206 advantageously enhances the distal pushability of the device, particularly when the device is advanced though an occlusion.

Upon positioning the distal end of wire 205 at a location distal to the occlusion, sheath 206 is retracted proximally to cause wire 205 to self-deploy to a knot-shaped configuration, as depicted in FIG. 6F. Coil 207, affixed to ball 208 of wire 205, conforms to the shape of wire 205. The deployed knot-shaped device then is proximally retracted to snare the occlusion, according to methods described hereinabove.

Figure 7A:
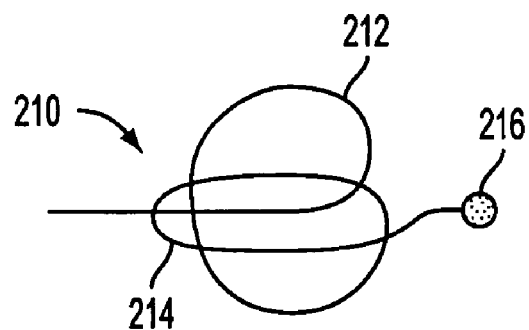
FIGS. 7A–7E illustrate alternative configurations for the thrombectomy wire of FIGS. 6.
Figure 7B:
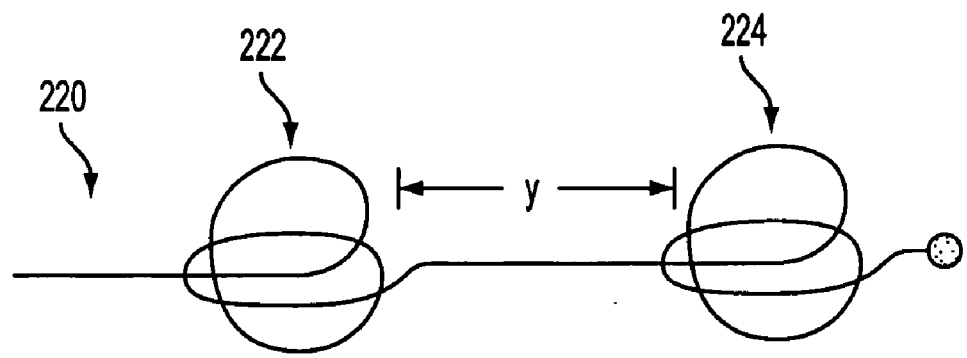

Referring to FIGS. 7A–7E, alternative embodiments for thrombectomy wires in accordance with the present invention are depicted. In FIG. 7A, thrombectomy wire 210 comprises a plurality of intersecting hoops that deploy upon retraction of a coil or sheath. Hoops 212 and 214 may be orthogonal to each other, as shown in FIG. 7A. The hoops are designed to form a knot-shape to snare a thrombus in combination with ball 216. Additionally, there may be a series of intersecting hoops, as shown in FIG. 7B. Thrombectomy wire 220 comprises first knot 222 and second knot 224 separated by a distance 'y', although it will be obvious that any variation in the number of knots and their shapes are intended to fall within the scope of the present invention.

Figure 7C:
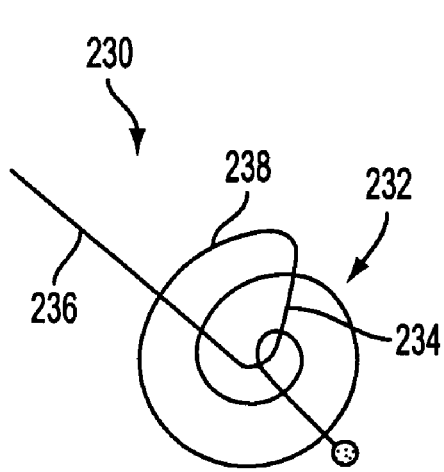
Figure 7D:
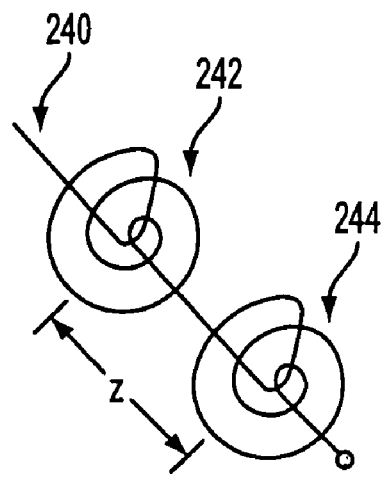

Referring to FIG. 7C, thrombectomy wire 230 comprises spiral-shaped distal section 232. The spiral shape is formed from a series of planar hoops, the diameter of hoops being slightly smaller with each successive hoop. As shown, the hoops of spiral 232 are depicted as being orthogonal to the main axis of wire 230. Elbow 234 defines a bent section that connects main wire section 236 to first hoop 238. As shown, elbow 234 is orthogonal to main wire section 236, however, it may be provided at any angle. Similarly, as shown in FIG. 7D, wire 240 may comprise a plurality of spiral-shaped sections 242 and 244 separated by a distance 'z'.

Figure 7E:
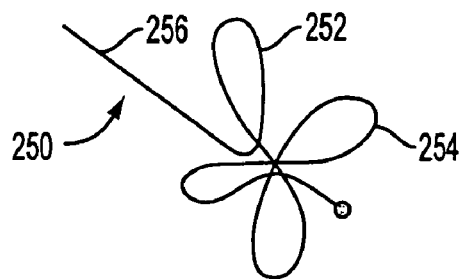

In FIG. 7E, thrombectomy wire 250 comprise a plurality of petal-shaped sections that deploy upon retraction of a coil or sheath. As shown, petal-shaped sections 252 and 254 are orthogonal to each other, however, they may be provided at any angle with respect to main axis 256 and each other, and any number of petal-shaped sections may be provided.

Referring to FIGS. 8A–8D, a further alternative thrombectomy device is illustrated. Device 260 removes a lesion by organizing the fibrin strands of the lesion around the deployable wires using a rotational motion. Exemplary method steps for using the embodiments described in FIGS. 8A–8D are described in FIGS. 10 hereinbelow.

Figure 8A:
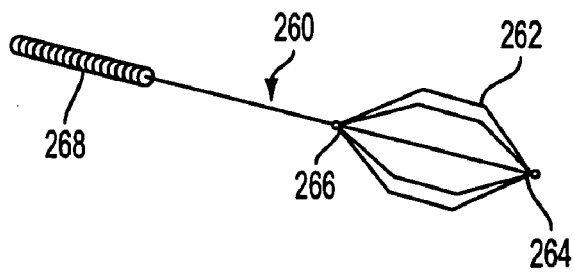
FIGS. 8A–8D illustrate thrombectomy wires configured to engage the fibrin strands of a thrombus.

In FIG. 8A, thrombectomy device 260 comprises at least one deployable wire 262 affixed at its proximal and distal ends at points 266 and 264, respectively. Deployable wire 262 is initially contracted within coil 268, and when tubular member 268, e.g., a coil or sheath, is retracted proximally, deployable wires 262 self-expand to a predetermined shape, as shown. As deployable wires 262 are rotated within the thrombus itself, the fibrin strands of the thrombus will become engaged with and wrap around deployable wires 262.

Figure 8B:
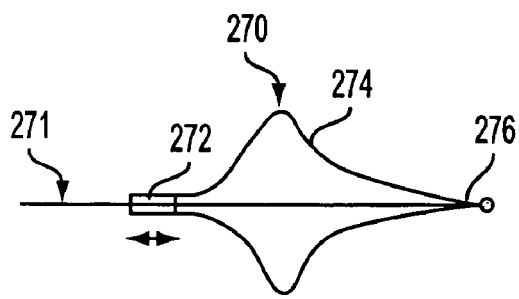

In FIG. 8B, alternative thrombectomy device 270 comprises at least one deployable wire 274 that is distally affixed to wire 270 at point 276. The proximal end of wire 274 is secured to sliding member 272, which slides longitudinally over wire 271. When wire 271 and sliding member 272 move with respect to each other, deployable wire 274 either radially outwardly deflects, as shown, or flattens out for a contracted position.

Figure 8C:
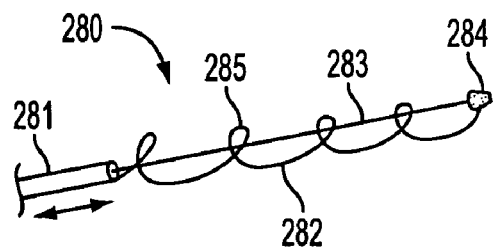

In FIG. 8C, thrombectomy device 280 comprises deployable wire 282 configured to form a plurality of loops 285 around shaft 283. The distal end of deployable wire 282 is affixed to shaft 283 at point 284, which may serve as an atraumatic tip for guiding the device and piercing the thrombus. The proximal end of deployable wire 282 is affixed to tube 281. Tube 281 spans the length of the device and has a proximal end that is manipulated by the physician. Distally advancing tube 281 over shaft 283 deploys loops 285, as shown, while proximally retracting tube 281 with respect to shaft 283 contracts loops 285. In the deployed state, rotating the device about its axis will cause loops 285 of wire 282 to engage the thrombus and wrap the fibrin strands about the device, as described in FIGS. 10 hereinbelow.

Figure 8D:
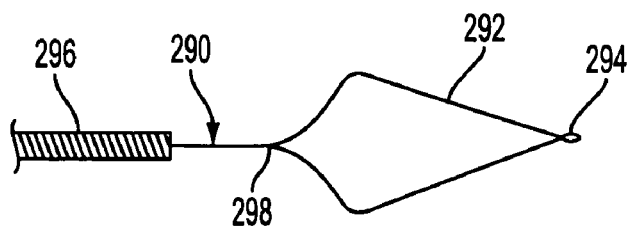

In FIG. 8D, thrombectomy device 290 comprises a plurality of shape-memory, arrowhead-shaped wires 292 that are distally affixed to each other at point 294 and proximally affixed at junction 298. Wires 292 are initially contracted within tubular member 296, e.g., a coil or sheath, and upon proximal retraction of tubular member 296, wires 292 self-deploy to the configuration shown.

Figure 9A:
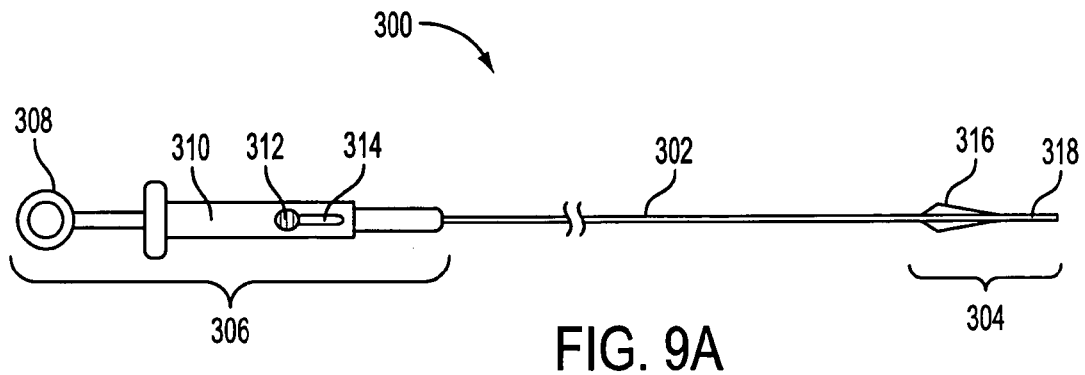
FIGS. 9A–9C describe an alternative thrombectomy device configured to engage the fibrin strands of a thrombus.

Apparatus and methods for organizing fibrin strands of a thrombus around a thrombectomy device are further described with respect to FIGS. 9 and 10. In FIG. 9A, thrombectomy device 300 comprises proximal segment 306, catheter 302, and distal segment 304. Proximal segment 306 comprises thumb ring 308, proximal body 310, and deployment knob 312 that slides longitudinally within slot 314. Distal segment 304 comprises at least one deployable wire 316 and atraumatic tip 318.

Figure 9B:
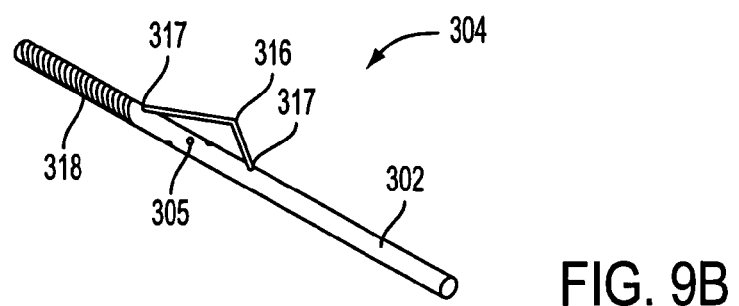

FIG. 9B provides a schematic view of distal segment 304. Deployable wire 316 preferably comprises a shape memory material that communicates with deployment knob 312 at its proximal end, as described in FIG. 9C hereinbelow. The distal end of deployable wire 316 is affixed to atraumatic tip 318, e.g., using a solder or weld. Deployable wire 316 is delivered in a contracted state, i.e., such that it does not substantially extend radially beyond catheter 302. Upon actuation of deployment knob 312, wire 316 self-expands via holes 317 to form a whisk-type element, as shown. Catheter 302 may be provided with one or more working lumens that communicate with delivery port 305 to permit the delivery of fluids, e.g., saline or other drugs that facilitate clot removal.

Figure 9C:
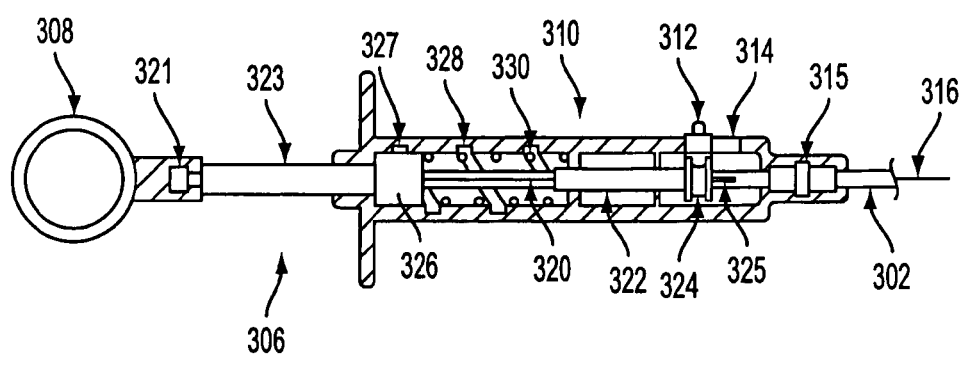

FIG. 9C provides a schematic view of proximal segment 306. The distal end of deployable wire 316 is configured to deploy from catheter 302. The proximal end of catheter 302 is affixed to outer shaft 322, which preferably has a square cross-section. Outer shaft 322 is keyed to inner shaft 320. Inner shaft 320 is keyed to slidably more actuator 323, so that rotational motion of one element causes rotation of the other. Catheter 302 further is affixed to retainer 315, which permits catheter 302 to rotate freely relative to proximal body 310.

Thumb ring 308 communicates with actuator 323 via joint 321. Joint 321 permits rotational motion of actuator 323 with respect to thumb ring 308. Actuator 323 is affixed to rotational member 326 at its distal end, which in turn is affixed to inner shaft 320. Rotational member 326 comprises knob 327 that is configured to slidably rotate within groove 328 in the wall of body 310.

Deployable wire 316 is deployed by sliding deployment knob 312 within slot 314. Deployment knob 312 comprises a rounded pin that engages with a groove of ring 324. This engagement distally advances ring 324 within slot 325 of catheter 302. Deployable wire 316 is affixed to ring 324, such that distally advancing ring 324 via deployment knob 312 allows wire 316 to self-deploy. The rounded pin engagement between knob 312 and the groove of ring 324 further permits free axial rotation of ring 324 while knob 312 is stationary.

With wire 316 deployed, thumb ring 308 is depressed with a force that overcomes a resistance force provided by spring 330. Depressing thumb ring 308 in turn causes rotational member 326 to be advanced distally via groove 328. When a thumb force is no longer applied, the resistance of spring 330 then pushes rotating member 326 in a proximal direction via groove 328. This in turn causes rotation of rotational member 326, inner shaft 320, outer shaft 322 and catheter 302. The rotation of catheter 302 generates rotation of thrombectomy wire 316.

The rotation of thrombectomy wire 316 may be clockwise, counterclockwise, or a combination thereof by manipulating the profile of groove 328. The rotational speed may be controlled by varying the resistance of spring 330, and the duration of rotation can be controlled by varying the length in which rotational member 326 can longitudinally move. Alternatively, another force transmission means, e.g., a motor, may be coupled to the proximal end to provide for controlled axial rotation of catheter 302.

FIGS. 10 illustrate method steps for removing thrombi using any of the thrombectomy devices described in FIGS. 8–9. In a first step, catheter 302 is advanced through catheter 2 of FIG. 2, then advanced in a retrograde fashion toward the occlusion. Catheter 302 may be advanced via the internal carotid artery to treat a lesion T located in a cerebral vessel V, e.g., the middle cerebral artery. Atraumatic tip 318 serves to protect vessel walls as catheter 302 is advanced through tortuous anatomy. At this time, flow control devices 8 of FIG. 2 are deployed to cause retrograde blood to flow in the directions indicated.

Figure 10A:
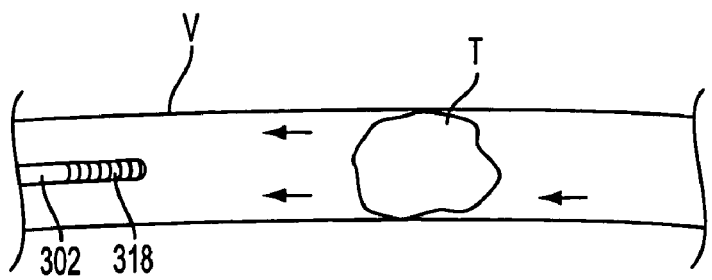
FIGS. 10A–10E illustrate method steps for removing an occlusion using the apparatus of FIGS. 9.
Figure 10B:
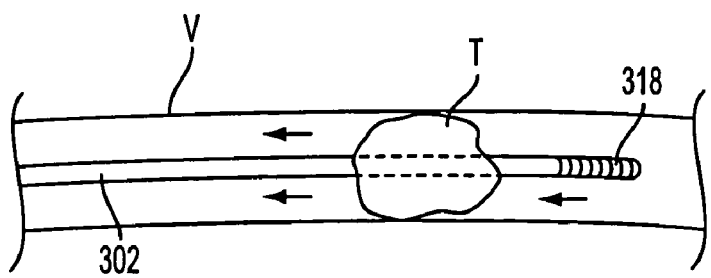
Figure 10C:
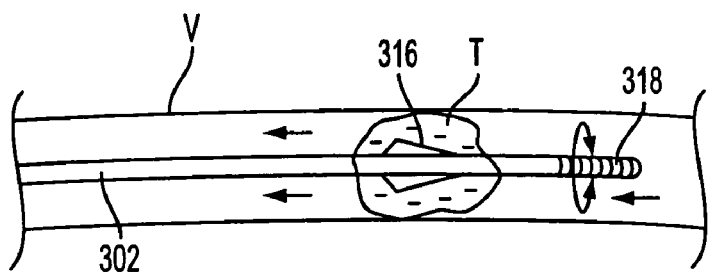
Figure 10D:
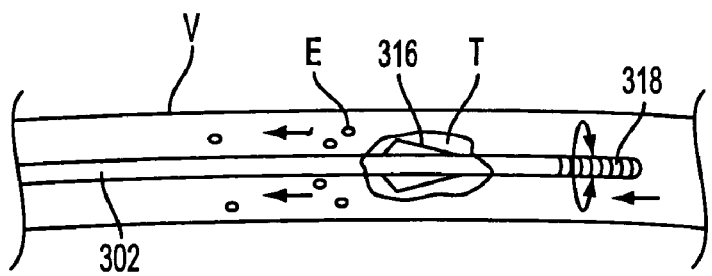
Figure 10E:
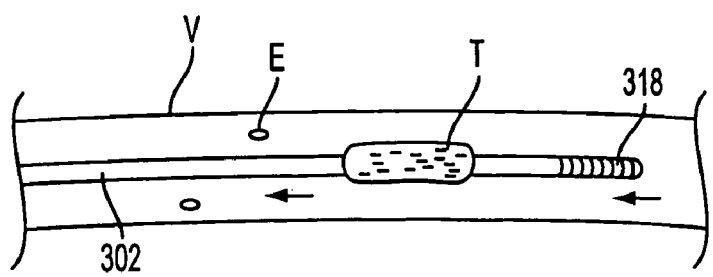

Tip 318 of catheter 302 then is advanced to pierce thrombus T, as shown in FIG. 10B. Deployment knob 312 of FIG. 9 then is actuated to deploy at least one deployable wire 316 within thrombus T. Thumb ring 308 then is depressed, resulting in the controlled rotation of deployable wire 316, such that the wire engages the fibrin strands of thrombus T. As the fibrin strands are wound about deployable wire 316, the diameter of thrombus T decreases, as shown in FIG. 10D. Blood flows in a retrograde fashion, i.e., toward catheter 2 which is positioned in the common carotid artery, and any emboli E generated during the procedure will be removed by the catheter in the process. It should be noted that deployable wire 316 is designed such that it does not contact the inner wall of vessel V. Once the thrombus T is sufficiently wound about deployable wire 316, as shown in FIG. 10E, catheter 302 may be retracted into catheter 2.

Figure 11:
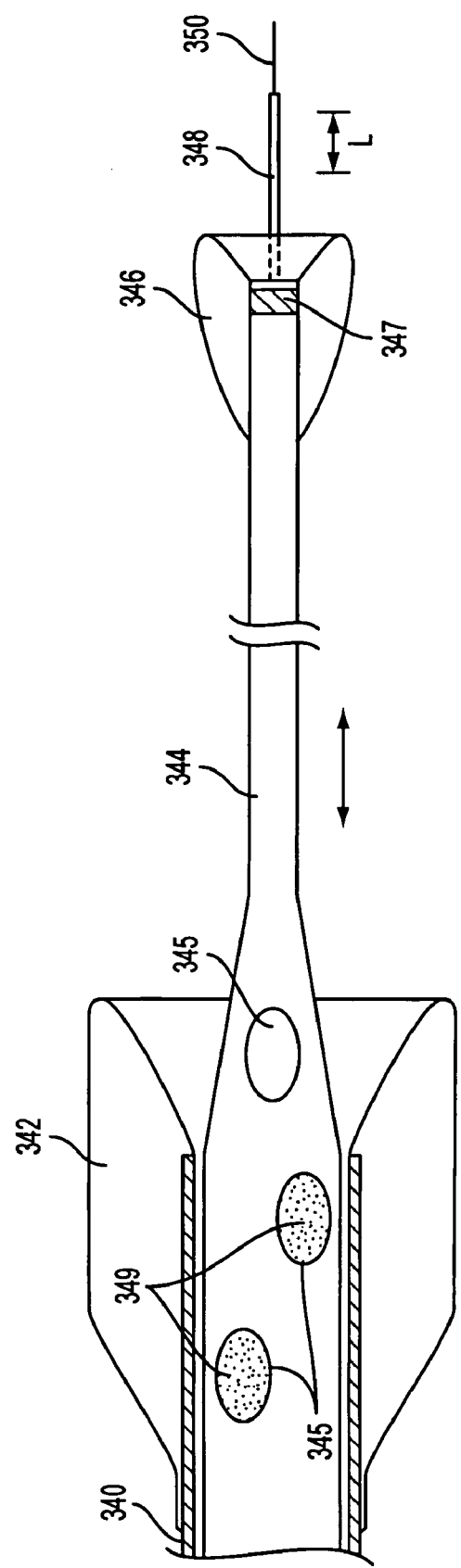
FIG. 11 describes a telescoping catheter configured to be advanced through the main catheter.

Referring to FIG. 11, an alternative embodiment of the present invention is described wherein a second catheter is advanced to a location in closer proximity to the occlusive lesion. Main catheter 340 having distal occlusive element 342 is positioned, for example, in the common carotid artery, as described in FIG. 2. Recovery catheter 344 having distal occlusive element 346 and radiopaque marker 347 is configured to telescope within the lumen of main catheter 340.

In a preferred method, main catheter 340 is disposed in the common carotid artery. Retrograde flow then is established using venous return line 52 of FIG. 3A according to methods described hereinabove. A 0.014 inch neuro guidewire 350 then is advanced via the lumen of main catheter 340 to the site of the cerebral occlusion, and neuro guidewire 350 is disposed distal to the lesion. In this illustration, an occlusion (not shown) would be located approximately within an interval 'L', e.g., in the middle cerebral artery. Recovery catheter 344 then is advanced distally over neuro guidewire 350 and is positioned proximal to occlusion 'L'. Upon positioning recovery catheter 344, occlusive distal element 346 is deployed.

Neuro catheter 348 then is advanced over neuro guidewire 350, and the distal end of neuro catheter 348 is disposed at a location distal to occlusion 'L', as shown. Neuro guidewire 350 then is retracted proximally and removed from within neuro catheter 348, which comprises a relatively small lumen. With neuro guidewire 350 removed, a thrombectomy wire is advanced distally through the lumen of neuro catheter 348, and the thrombectomy wire takes the place of guidewire 350 in FIG. 11. Neuro catheter 348 then is proximally retracted, and thrombectomy wire 350 is deployed to treat the occlusion according to methods described hereinabove.

Recovery catheter 344 comprises at least one blood venting hole 345. The established retrograde flow through catheter 344 using venous return line 52 induces retrograde flow in at least the internal carotid artery via blood venting hole 345. Flow into venting hole 345 may be manipulated by actuating inner sheath 349, e.g., by longitudinally sliding inner sheath 349 within catheter 344, or rotating inner sheath 349 relative to its longitudinal axis.

Advantageously, the distal end of recovery catheter 344 is positioned in close proximity to the lesion, so that wire 348 and any emboli generated are immediately confined within recovery catheter 344. Furthermore, advancing recovery catheter 344 via the internal carotid artery eliminates the need for deploying balloon 10 of FIG. 2 in the external carotid artery.

Referring to FIGS. 12, a further alternative embodiment of the present invention is described wherein a second catheter is advanced to a location in closer proximity to the occlusive lesion. Main catheter 360 having distal occlusive element 362 is positioned, for example, in the common carotid artery, as described in FIG. 2. Recovery catheter 364 comprises a wire weave configuration and may be manufactured using a shape memory material, e.g., Nitinol, as described hereinabove.

Recovery catheter 364 further comprises blood impermeable membrane 365, such as latex, polyurethane or polyisoprene, that encloses the wire weave of recovery catheter 364. The elastic properties of blood impermeable membrane 365 allow it to conform to the contracted and expanded states of recovery catheter 364.

Figure 12A:
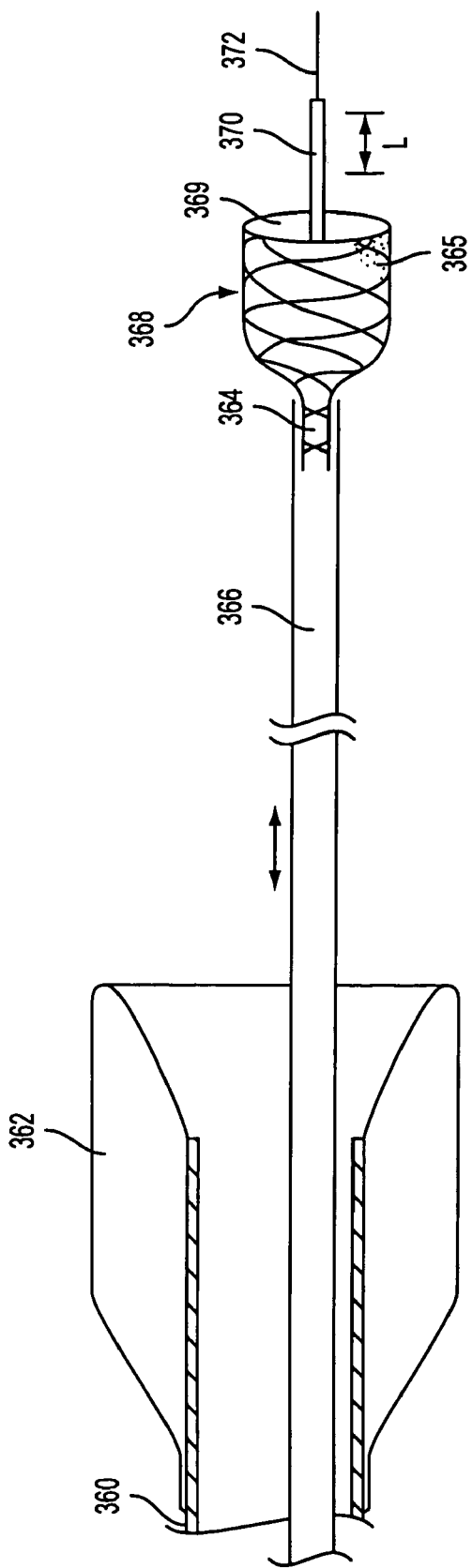
FIGS. 12A–12D describe a telescoping catheter having an expandable distal section configured to be advanced through the main catheter.

Recovery catheter 364 is advanced in a contracted state within outer sheath 366. As described in applicants' commonly assigned, co-pending application Ser. No. 09/916, 349, which is herein incorporated by reference, outer sheath 366 is retracted proximally to cause occlusive distal section 368 to self-expand to a predetermined deployed configuration, as shown in FIG. 12A. Occlusive distal section 368 may be sized for different vessels, e.g., the middle cerebral arteries, so that the distal end of recovery catheter 364 is disposed proximal to an occlusion, e.g., as depicted at location 'L'. Mouth 369 provides a relatively large distal opening, i.e., flush with the inner wall of the targeted vessel.

Neuro catheter 370 then is advanced over neuro guidewire 372, as described hereinabove in FIG. 11, and a thrombectomy wire is exchanged for neuro guidewire 372. Neuro catheter 370 is proximally retracted, and thrombectomy wire 372 removes the occlusion at location 'L' according to methods described hereinabove. Upon removing the occlusion, thrombectomy wire 372 is retracted into mouth 369, along with any emboli generated during the procedure.

Figure 12D:
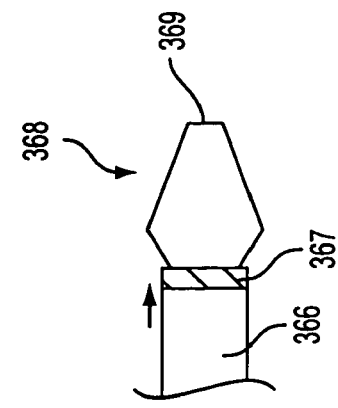
Figure 12C:
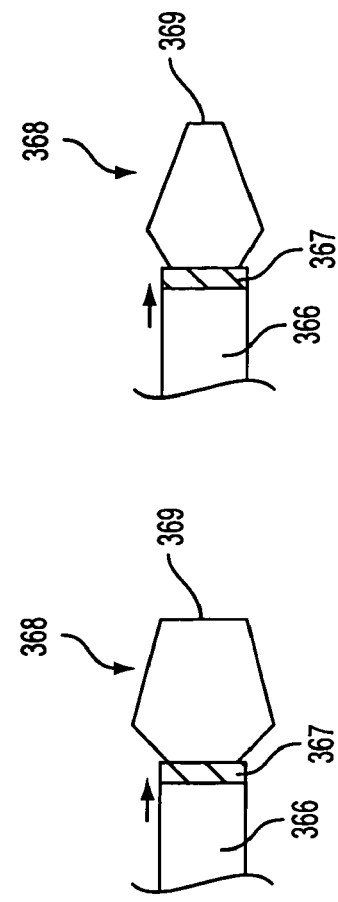
Figure 12B:
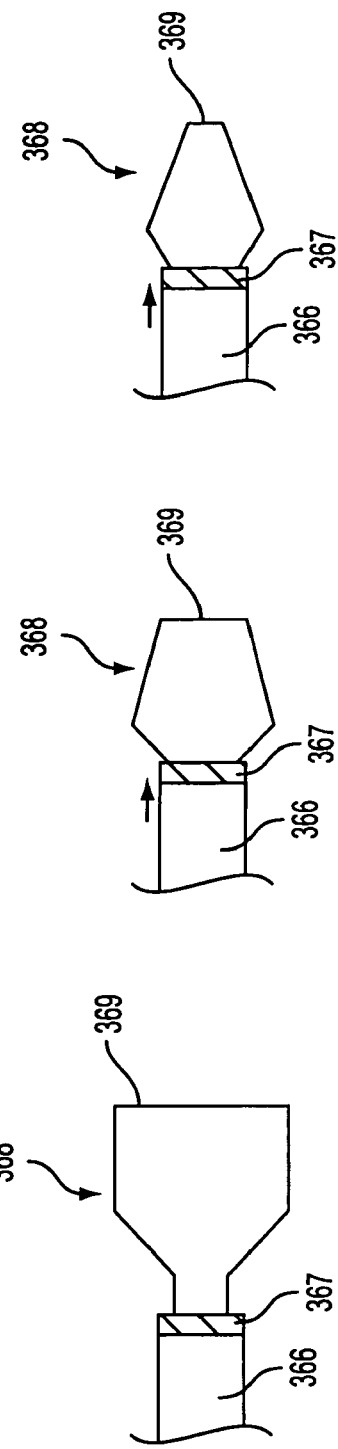

It will be advantageous to collapse mouth 369 upon completion of the procedure, to prevent thrombi and/or emboli from exiting removal catheter 364. FIGS. 12B–12D illustrate a method for effectively collapsing mouth 369 proximally to distally, as shown. FIG. 12B shows outer sheath 366 having radiopaque marker 367 in a proximally retracted position that allows occlusive distal section 368 to deploy. After directing thrombi and/or emboli into mouth 369, outer sheath 366 is advanced distally to collapse mouth 369, as shown sequentially in FIGS. 12C–12D. This effectively confines thrombi and/or emboli within mouth 369.

Referring now to FIGS. 13, a method for using the apparatus described hereinabove to treat stroke, in accordance with principles of the present invention, is described. In FIG. 13A, flow control devices 400 having controllers 402 are introduced into the patient's vasculature in a contracted state, e.g., via the radial or brachial arteries, and preferably are positioned in the patient's left subclavian artery and brachiocephalic trunk, as shown. It will be appreciated by those skilled in the art that varying the number of flow control devices and their placements is intended to fall within the scope of the present invention. Blood flow occurs in the directions indicated.

Figure 13A:
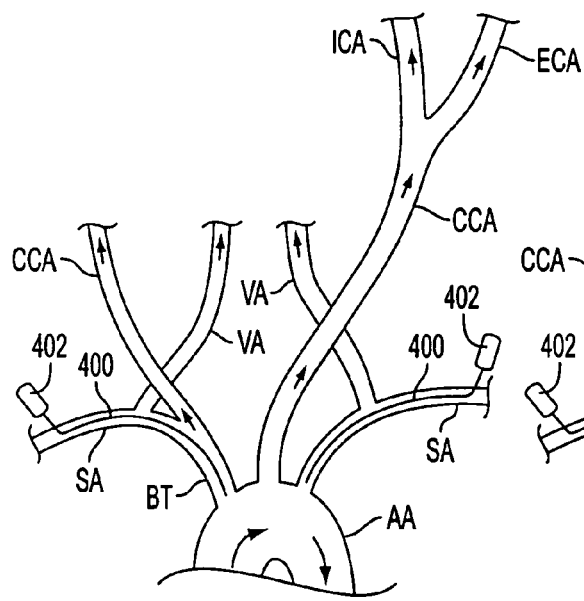
FIGS. 13A–13H illustrate method steps for controlling cerebral blood flow and removing thrombi and/or emboli in accordance with the present invention.
Figure 13B:
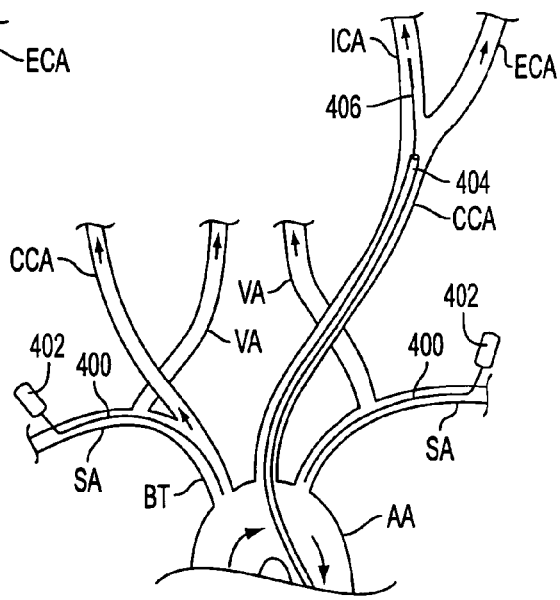
Figure 13C:
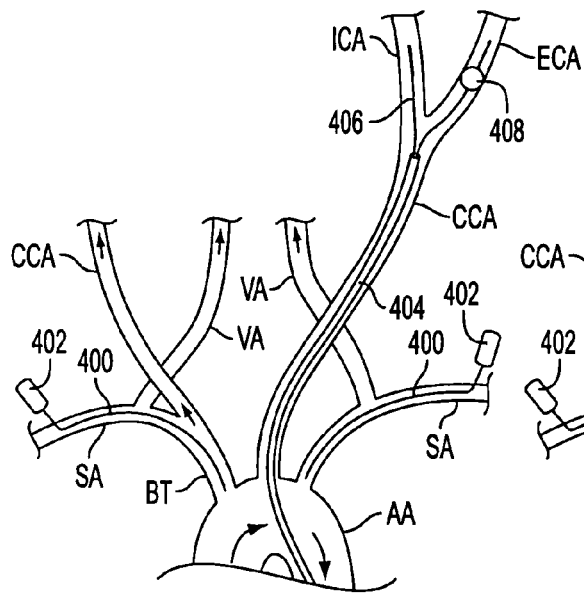

Referring to FIG. 13B, catheter 404 of FIG. 3A is positioned in the common carotid artery CCA using guide wire 406. Catheter 404 is positioned proximal to the carotid bifurcation, as shown, preferably in the hemisphere in which the cerebral occlusion is located. Balloon 408, for example, as described in FIGS. 5, then is disposed in the external carotid artery and deployed, as shown in FIG. 13C.

Figure 13D:
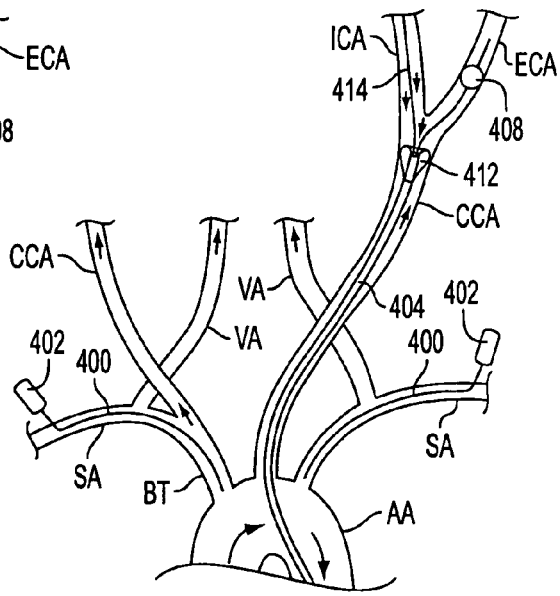

Referring to FIG. 13D, distal occlusive element 412 of catheter 404 is deployed to occlude antegrade flow in the selected CCA. Venous return catheter 52 of FIG. 3A then is placed in a remote vein, such that negative pressure in venous return catheter 52 during diastole establishes a continuous flow through the lumen of catheter 404. This induces retrograde flow in the ICA, as depicted in FIG. 13D. A thrombectomy wire 414, for example, as described in FIGS. 6–10, is advanced through catheter 404 and into the cerebral vasculature via the ICA.

Figure 13E:
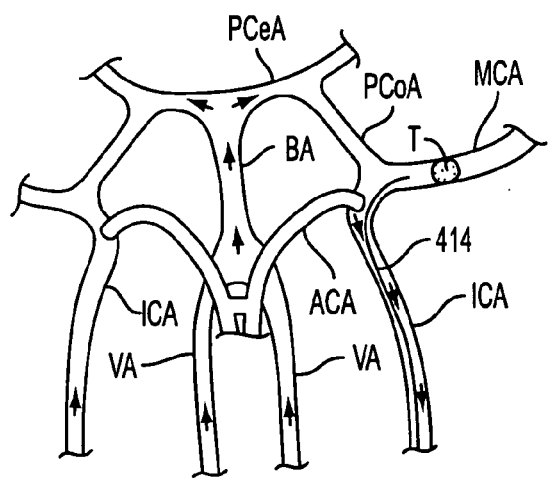

Referring to FIG. 13E, a view of the cerebral vasculature under the conditions described in FIG. 13D is shown. Thrombectomy wire 414 has been advanced to a location just proximal to thrombus T, for example, in middle cerebral artery MCA.

Figure 13F:
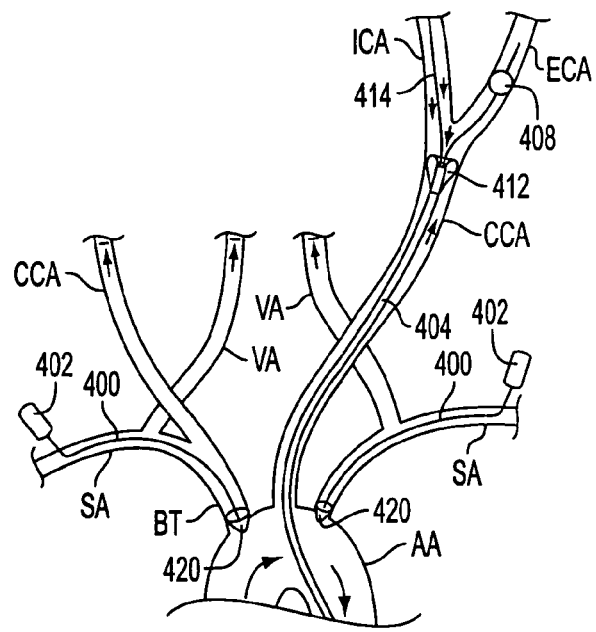

At this time, flow control devices 400 then are deployed using controller 402 to form occlusive elements 420, as shown in FIG. 13F. As depicted, flow from aortic arch AA into brachiocephalic trunk BT and left subclavian artery SA are inhibited, which in turn inhibits flow into the vertebral arteries VA and right CCA, as shown. It will be apparent to those skilled in the art that occlusive elements 420 may be selectively placed at other locations to permit and/or inhibit flow into the selected locations of the cerebral vasculature.

Figure 13G:
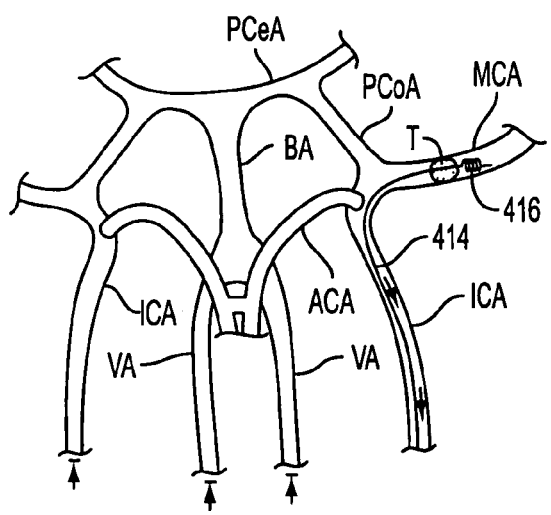

The deployment of occlusive elements 420 controls flow in the Circle of Willis, as shown in FIG. 13G. In this example, since arterial flow into the vertebral arteries VA and the right internal carotid artery has been inhibited, emboli that are generated will be directed in a retrograde fashion toward catheter 404 via the left internal carotid artery. The distal end of thrombectomy wire 414 then pierces thrombus T and deployable knot 416 is deployed distal to the thrombus, as shown in FIG. 13G. Alternatively, other thrombectomy wire configurations may be used to treat the lesion, as described in FIGS. 6–10.

Figure 13H:
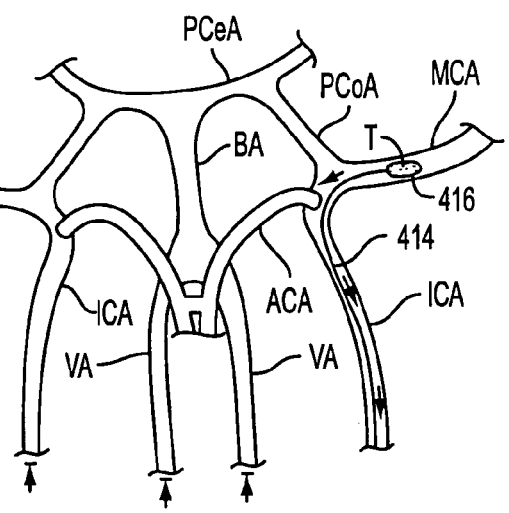

Deployable knot 416 of thrombectomy wire 414 snares thrombus T, as shown in FIG. 13H, and subsequently is retracted into catheter 404. Any emboli generated during the procedure will be directed into catheter 404 via the established retrograde flow. Occlusive elements 420, distal occlusive element 412, and external carotid occlusive device 408 then are contracted, and catheter 404 may be removed from the patient.

It should be noted that the method steps described in FIGS. 13 may be used in combination with any of the apparatus described hereinabove. For example, recovery catheters 344 and 364 of FIGS. 11 and 12, respectively, may be advanced through catheter 404 of FIGS. 13. Additionally, any of the snaring thrombectomy devices of FIGS. 7 or the rotating thrombectomy devices of FIGS. 8 may be used in place of thrombectomy wire 414 as depicted. Similarly, any of the occlusive devices described in FIGS. 4B–4E and FIGS. 5A–5B may be used in place of occlusive elements 420 and 408, respectively.

Figure 14A:
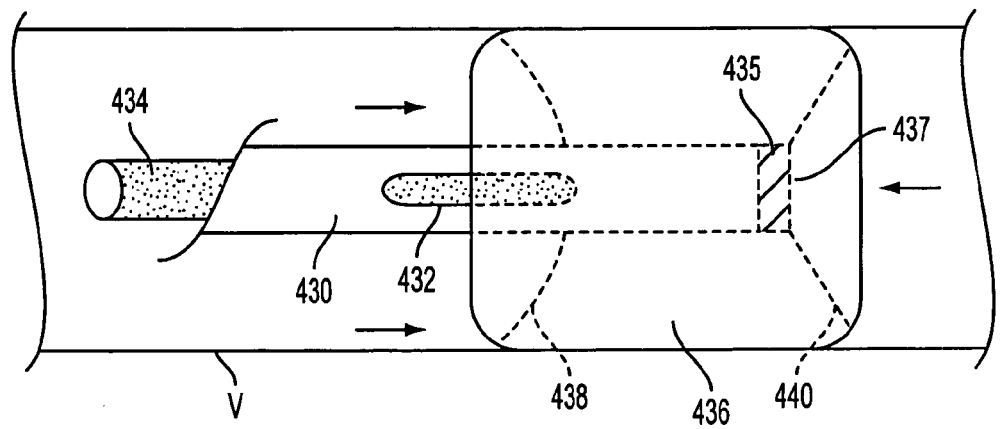
FIGS. 14A–14B describe a catheter having an intake port configured to provide for retrograde and/or antegrade flow in either of the carotid or vertebral arteries.
Figure 14B:
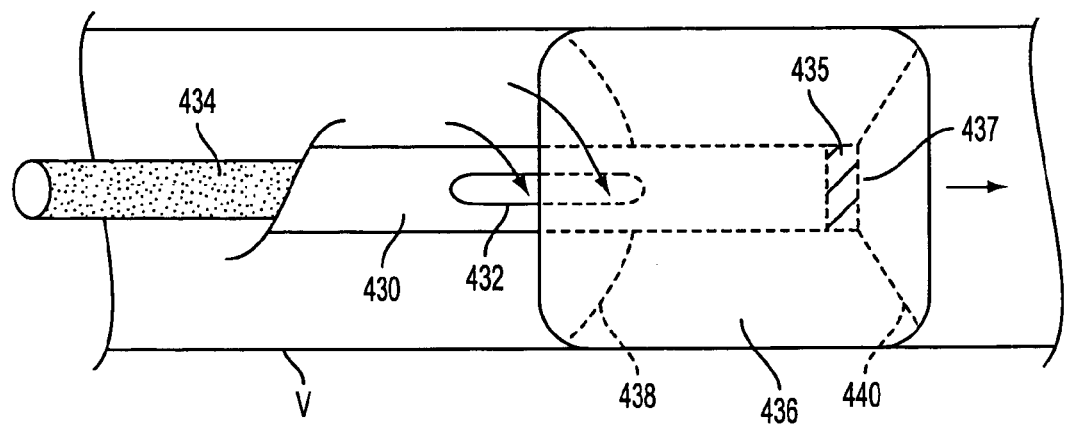
Figure 15:
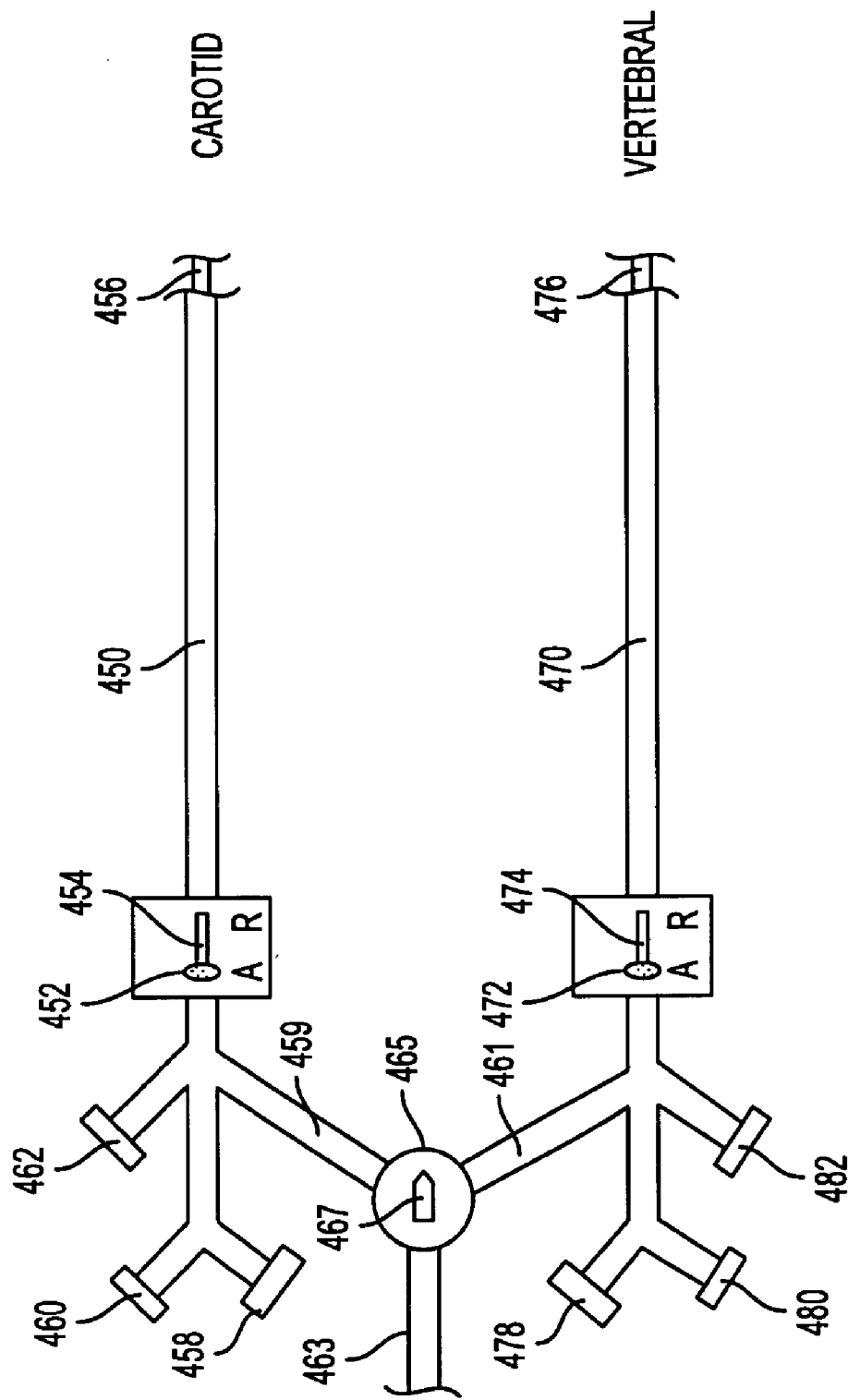
FIG. 15 illustrates a proximal assembly suitable for controlling retrograde and antegrade flow in the carotid and vertebral catheters of FIG. 14.

Referring to FIGS. 14–16, further apparatus and methods is accordance with principles of the present are described. In FIG. 14A, catheter 430 may be configured for use in any of the carotid and vertebral arteries. Catheter 430 comprises blood intake port 432, distal occlusive element 436 and radiopaque tip marker 435. Occlusive element 436 comprises proximal and distal tapers 438 and 440, respectively. Inner sheath 434 is configured for longitudinal sliding motion within catheter 430.

Inner sheath 434 is initially provided in a distalmost position that covers blood intake port 432 in a closed state, as shown in FIG. 14A. Deployment of occlusive element 436 inhibits antegrade blood flow in vessel V, at which time therapeutic drugs and/or devices may be delivered to site of the occlusion via lumen 437.

Retrograde blood flow in vessel V is induced by placing venous return catheter 52 of FIG. 3A into a remote vein, according to methods described hereinabove. The retrograde flow through lumen 437 induces retrograde flow distal to occlusive element 436. Distal taper 440 facilitates retrograde blood flow into lumen 437.

If antegrade flow is desired, inner sheath 434 may be retracted proximally to expose blood intake port 432, as shown in FIG. 14B. This permits antegrade flow to enter intake port 432 and continue flowing in an antegrade direction distal to occlusive element 436. Proximal taper 438 is configured to enhance antegrade blood flow into intake port 432.

Cerebral flow manipulation may be enhanced by placing a first catheter in accordance with FIGS. 14 in a common carotid artery and a second catheter in a vertebral artery, each on the hemisphere of the occlusion. FIG. 15 depicts apparatus suitable for controlling cerebral flow when utilizing one carotid and one vertebral catheter in combination. In FIG. 15, catheters 450 and 470 are configured to be disposed in the common carotid and vertebral arteries, respectively. However, it should be appreciated by those skilled in the art that two vertebral catheters may be used, i.e., one in each of the vertebral arteries, in combination with the carotid catheter.

Catheters 450 and 470 each comprises a plurality of lumens. Inner sheaths 456 and 476 are configured to slide longitudinally within an outermost lumen of their respective catheters. Inner sheaths 456 and 476 communicate with deployment knobs 452 and 472. Sliding deployment knobs 452 and 472 within slots 454 and 474 controls movement of inner sheaths 456 and 476, respectively.

Inflation ports 462 and 482 communicate with lumens of their respective catheters. Working lumens 458, 460, 478 and 480 provide each catheter with two working lumens, e.g., for advancing guide wires and thrombectomy wires, and may be provided with hemostatic valves, for example, Touhy-Borst connectors.

Biocompatible tubing 459 and 461 enable fluid communication between retrograde flow controller 465 and lumens of catheter 450 and 470, respectively. Retrograde flow controller 465 further communicates with venous return line 52 of FIG. 3A via tubing 463. Switch 467 of retrograde flow controller 465 permits tubing 459 and 461 to communicate with retrograde flow of tubing 463 singularly or in combination, or switch 467 may inhibit retrograde flow altogether. For example, when retrograde flow is induced in tubing 463 via venous return line 52, either one of tubing 459 and 461, both, or neither may experience retrograde flow based on the position of switch 467.

The apparatus described in FIG. 15 allow a physician to provide either retrograde, antegrade or hemostatic flow from two opposing cerebral locations, i.e., the carotid and vertebral arteries. The lumens of the vertebral and/or carotid catheters may be perfused with blood or saline under pressure to manipulate flow at selected cerebral locations. The apparatus further allows for the injection of therapeutic drugs and/or thrombectomy devices. Chilled blood or saline may be delivered via either of the carotid and vertebral catheters to induce mild hypothermia at selected cerebral locations, while drug agents may be used to selectively alter the pressure gradients.

Additionally, lytic agents may be delivered via either of the carotid or vertebral catheters to aid in the disintegration of the occlusion. Such lytic agents preferably are used in combination with the flow manipulation techniques in accordance with the present invention, to direct emboli resulting from the lytic process into the removal catheter(s).

Figure 16A:
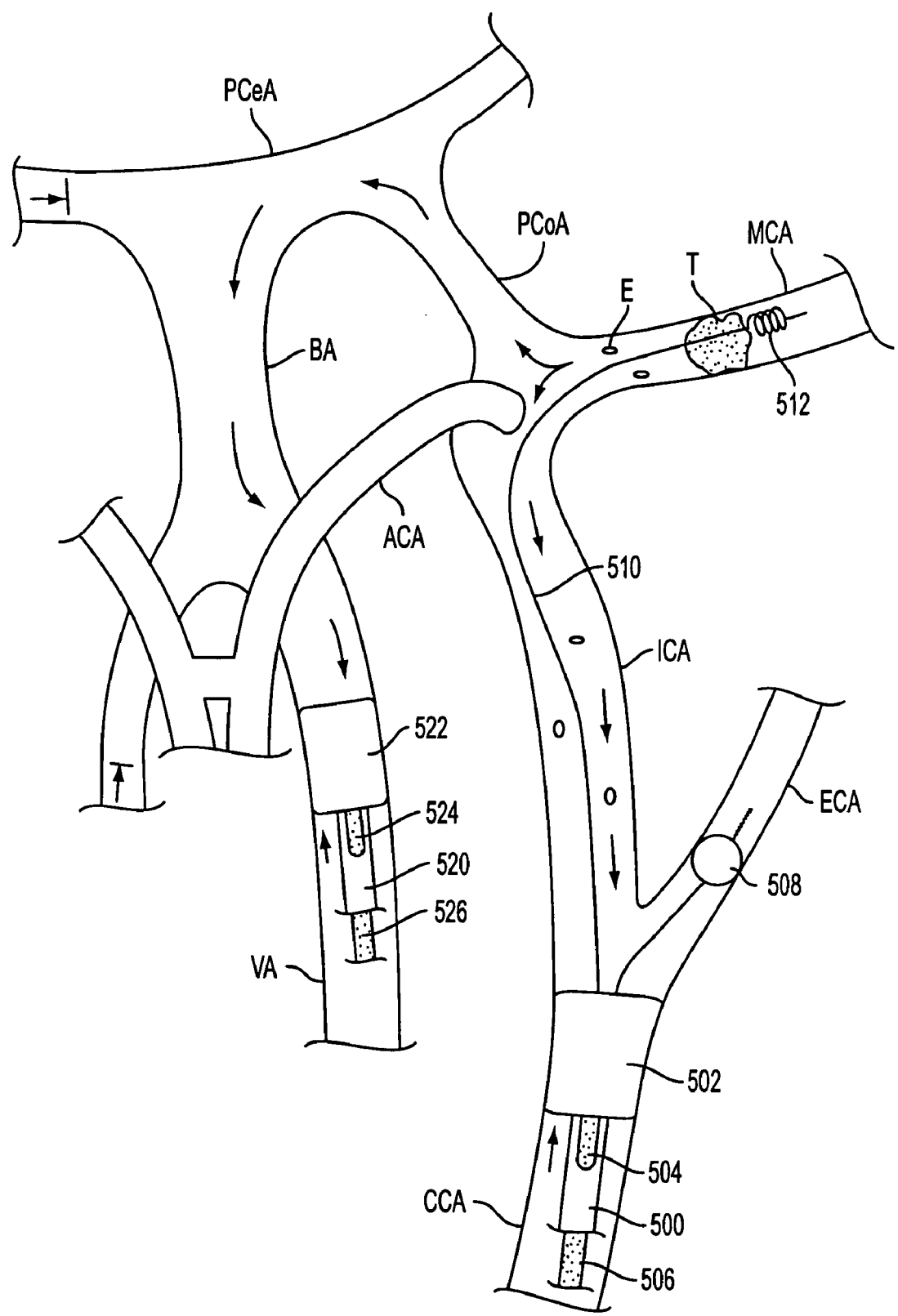
FIGS. 16A–16B provide examples of manipulating cerebral flow using a combination of carotid and vertebral catheters, each having antegrade and retrograde flow potential.

Referring to FIGS. 16, method steps are described to manipulate cerebral flow in a variety of ways using a combination of carotid and vertebral catheters. In FIG. 16A, a first catheter 500 comprising occlusive element 502 and blood intake port 504 is disposed in the left common carotid artery CCA. Inner sheath 506 is provided in a distalmost position to prevent fluid from entering intake port 504, and occlusive element 502 is deployed to occlude antegrade flow. Balloon 508, e.g., as described in FIGS. 5, then is deployed in the ECA.

Similarly, a second catheter 520 comprising occlusive element 522 and blood intake port 524 is disposed in the left and/or right vertebral artery VA. In this example, one catheter is shown. Inner sheath 526 is provided in a distalmost position to prevent fluid from entering intake port 544, and occlusive element 522 is deployed to occlude antegrade flow.

Venous return line 52 of FIG. 3A then is placed in a remote vein, according to methods described hereinabove, and retrograde flow may be induced either in the ICA, VA, or both arteries based on switch 467 of FIG. 15. As depicted in FIG. 16A, switch 467 is set to a position that permits retrograde flow to be induced in both the carotid and vertebral catheters.

At this time, any of the flow control devices described in FIGS. 4 optionally may be deployed to occlude flow in the opposing carotid and vertebral arteries, according to methods described hereinabove. In this example, this ensures that blood flow is controlled in the left hemisphere.

The retrograde flow from catheters 500 and 520 encourages blood flowing in the middle cerebral artery MCA to flow toward both catheters, as indicated by the arrows in FIG. 16A. Thrombectomy wire 510 having deployable knot 512 then is advanced into the MCA via the ICA and snares thrombus T, according to methods described hereinabove. Emboli E generated during the procedure are directed toward either one of catheters 500 and 520 for removal. Advantageously, the use of two catheters in combination provides for improved aspiration of the targeted vessel, in this case, the MCA.

Figure 16B:
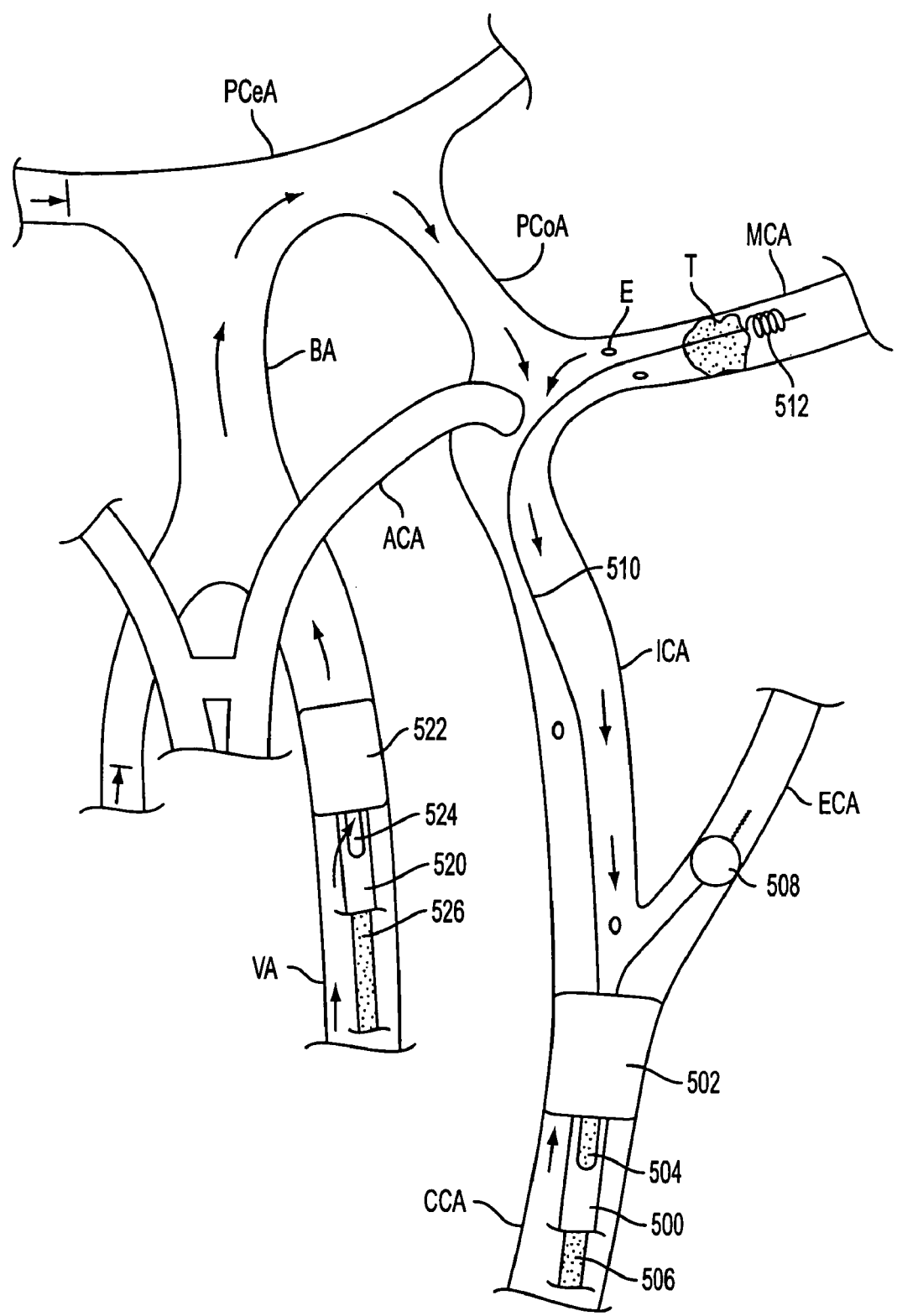

Referring to FIG. 16B, deployable knob 472 of FIG. 15 is proximally retracted to retract inner sheath 526 and expose intake port 524 of catheter 520. Switch 467 of retrograde flow controller 465 is positioned for retrograde flow only through catheter 500. This allows antegrade flow in vertebral artery VA to enter intake port 524 and continue flowing in an antegrade direction into basilar artery BA and toward the MCA via the path indicated. The combination of antegrade flow from the left VA and either antegrade or retrograde flow from the left ICA directs emboli E generated in the MCA to flow primarily into catheter 500.

There are several other variations possible for manipulating flow in the cerebral vasculature, to more efficiently deliver therapeutic drugs and/or direct emboli into a removal catheter. For example, therapeutic drugs may be delivered to the MCA when switch 467 of FIG. 15 inhibits venous flow into both catheters 500 and 520, and each of blood intake ports 504 and 524 are closed. Therapeutic drugs may be delivered via either port 458 or 478 into the MCA, or mild hypothermia may be induced by introducing chilled blood or saline.

It should be appreciated that varying the settings of retrograde flow controller 465 and deployable knobs 452 and 472 may provide for any combination of antegrade, retrograde, or hemostatic flow in the carotid and vertebral arteries. There are too many flow combinations to illustrate, however, it is intended that therapeutic drugs, thrombectomy devices, cardioplegic and/or brain chilling agents may be delivered under a variety of controlled cerebral flow conditions. Additionally, a neuro guidewire and neuro catheter, as described in FIGS. 11 and 12A hereinabove, may be used in conjunction with thrombectomy wire 510 of FIGS. 16.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus suitable for manipulating cerebral blood flow characteristics, the apparatus comprising:
a catheter having proximal and distal ends, a lumen extending therebetween, and an occlusive element affixed to the distal end, the occlusive element having an opening that communicates with the lumen, the occlusive element having a contracted position (configured for transluminal retrograde insertion via the descending aorta and an expanded position wherein the occlusive element occludes antegrade flow in a carotid artery;) and
a flow control device having proximal and distal ends and a flow control element disposed at the distal end, (the flow control device configured for insertion, separately from the catheter, via a subclavian artery brachiocephalic trunk so that the flow control device, when deployed, inhibits flow to vertebral and common carotid arteries, thereby controlling mid-cerebral artery flow.

2. The apparatus of claim 1 wherein the occlusive element comprises an inflatable balloon.

3. The apparatus of claim 2 wherein the inflatable balloon further comprises a distal taper.

4. The apparatus of claim 3 wherein the inflatable balloon further comprises a proximal taper.

5. The apparatus of claim 1 wherein the flow control element is inflatable.

6. The apparatus of claim 1 wherein the flow control element comprises a plurality of deployable wires coated with a blood impermeable layer.

7. The apparatus of claim 1 wherein the occlusive element affixed to the catheter is configured to occlude antegrade flow in an artery.

8. The apparatus of claim 1 further comprising:
a shaft having proximal and distal ends; and
a balloon having proximal and distal ends, the balloon being disposed near the distal end of the shaft.

9. The apparatus of claim 8 wherein the balloon is adapted to be disposed in a communicating artery.

10. The apparatus of claim 8 wherein the distal end of the balloon is everted.

11. The apparatus of claim 10 wherein the proximal end of the balloon is everted.

12. The apparatus of claim 1 further comprising a recovery catheter having proximal and distal ends, the recovery catheter configured to telescope in and out of the first catheter.

13. The apparatus of claim 12 wherein the recovery catheter comprises a balloon affixed to the distal end.

14. The apparatus of claim 12 further comprising at least one venting hole disposed in a lateral surface of the recovery catheter.

15. The apparatus of claim 14 further comprising an inner sheath configured to manipulate flow into the venting hole.

16. The apparatus of claim 12 wherein the recovery catheter comprises a radially expandable distal section.

17. The apparatus of claim 16 wherein the radially expandable distal section comprises a wire weave configuration covered by an impermeable membrane.

18. A system for manipulating cerebral blood flow characteristics, the system comprising:
a catheter having proximal and distal ends, a lumen extending therebetween, and an occlusive element affixed to the distal end, the occlusive element having an opening that communicates with the lumen, a contracted position configured for transluminal retrograde insertion via the descending aorta and an expanded position wherein antegrade flow in a carotid artery is occluded; and
a flow control device, separate from the catheter, having a flow control element configured for insertion via a subclavian artery and brachiocephalic trunk so that the flow control device, when deployed, inhibits flow to vertebral and common carotid arteries, thereby controlling mid-cerebral artery flow.

19. The system of claim 18 wherein the occlusive element comprises an inflatable balloon.

20. The system of claim 19 wherein the inflatable balloon further comprises at least one of a proximal or distal taper.

21. The system of claim 18 wherein the flow control element is inflatable.

22. The system of claim 18 wherein the flow control element comprises a plurality of deployable wires coated with a blood impermeable layer.

* * * * *

UNITED STATES PATENT AND TRADEMARK OFFICE
CERTIFICATE OF CORRECTION

PATENT NO. : 7,063,714 B2
APPLICATION NO. : 09/972225
DATED : June 20, 2006
INVENTOR(S) : Dorros et al.

It is certified that error appears in the above-identified patent and that said Letters Patent is hereby corrected as shown below:

Column 17, line 56: remove "("

Column 17, line 60: remove ")"

Column 17, line 62: remove "("

Signed and Sealed this

Thirteenth Day of March, 2007

JON W. DUDAS
*Director of the United States Patent and Trademark Office*